US012788418B2

(12) United States Patent
Metcalfe et al.

(10) Patent No.: US 12,788,418 B2
(45) Date of Patent: Nov. 10, 2026

(54) PATIENT-SPECIFIC ORTHOPAEDIC TRANSFER GUIDES AND ASSOCIATED METHODS OF REPAIR

(71) Applicant: ARTHREX, INC., Naples, FL (US)

(72) Inventors: Nick Metcalfe, Bonita Springs, FL (US); Kevin John Gallen, Naples, FL (US); Dean Acker, Naples, FL (US); Steven Jim DeLeon, Naples, FL (US); Scott William Doody, Bonita Springs, FL (US); Mark Wise, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 19/204,708

(22) Filed: May 12, 2025

(65) Prior Publication Data

US 2025/0359874 A1 Nov. 27, 2025

Related U.S. Application Data

(60) Provisional application No. 63/651,530, filed on May 24, 2024.

(51) Int. Cl.

*A61B 17/17* (2006.01)
*A61B 90/00* (2016.01)
*A61B 17/00* (2006.01)

(52) U.S. Cl.

CPC .............. *A61B 17/17* (2013.01); *A61B 90/03* (2016.02); *A61B 90/08* (2016.02); *A61B 2017/00477* (2013.01); *A61B 2090/034* (2016.02); *A61B 2090/0807* (2016.02)

(58) Field of Classification Search

CPC ..... A61B 17/17; A61B 17/1778; A61B 34/25; A61B 2034/102; A61B 2034/105; A61B 2034/108; A61B 17/1684; A61B 17/8897; A61B 2017/00477; A61B 2017/568; A61F 2/30734; A61F 2/30942; A61F 2002/30736; A61F 2002/30738; A61F 2002/30878; A61F 2/4081; A61F 2/4603; A61F 2/4684

See application file for complete search history.

(56) References Cited

U.S. PATENT DOCUMENTS

| | | | |
|---|---|---|---|
| 5,133,660 | A | 7/1992 | Fenick |
| 8,496,663 | B2 | 7/2013 | White et al. |
| 8,623,026 | B2 | 1/2014 | Wong et al. |

(Continued)

FOREIGN PATENT DOCUMENTS

| | | |
|---|---|---|
| KR | 101863741 B1 | 6/2018 |
| KR | 101981055 | 5/2019 |
| KR | 102053599 | 1/2020 |

OTHER PUBLICATIONS

Botha, C.P. (2005). Techniques and software architectures for medical visualisation and image processing. ASCI dissertation series No. 117. pp. 1-180.

(Continued)

*Primary Examiner* — Anu Ramana
(74) *Attorney, Agent, or Firm* — Carlson, Gaskey & Olds, P.C.

(57) ABSTRACT

This disclosure relates to surgical systems, devices and methods for planning and implementing surgical procedures. The systems and methods disclosed herein may be utilized to establish surgical guides for positioning implants relative to the anatomy.

20 Claims, 32 Drawing Sheets

(56) References Cited

U.S. PATENT DOCUMENTS

| | | | |
|---|---|---|---|
| 8,808,302 B2 | 8/2014 | Roose et al. | |
| 9,125,674 B2 | 9/2015 | White et al. | |
| 9,125,675 B2 | 9/2015 | White et al. | |
| 9,232,955 B2 | 1/2016 | Bonin, Jr. et al. | |
| 9,265,511 B2 | 2/2016 | White et al. | |
| 9,326,780 B2 | 5/2016 | Wong et al. | |
| 9,498,233 B2 * | 11/2016 | Eash | A61F 2/4609 |
| 9,579,106 B2 | 2/2017 | Lo et al. | |
| 9,615,839 B2 | 4/2017 | Olson | |
| 9,839,438 B2 | 12/2017 | Eash | |
| 10,245,048 B2 | 4/2019 | Olson | |
| 10,426,549 B2 | 10/2019 | Kehres et al. | |
| 10,441,298 B2 | 10/2019 | Eash | |
| 10,624,655 B2 | 4/2020 | Iannotti et al. | |
| 10,813,774 B2 * | 10/2020 | Davenport | A61F 2/4609 |
| 10,842,512 B2 | 11/2020 | Bonin, Jr. et al. | |
| 11,045,208 B2 | 6/2021 | Park et al. | |
| 11,166,733 B2 * | 11/2021 | Neichel | A61F 2/4081 |
| 11,179,249 B2 * | 11/2021 | Deransart | A61F 2/4612 |
| 11,602,360 B2 | 3/2023 | Heilman et al. | |
| 11,617,591 B2 | 4/2023 | Eash | |
| 12,133,691 B2 | 11/2024 | Chaoui et al. | |
| 12,256,997 B2 * | 3/2025 | Metcalfe | A61F 2/30942 |
| 12,402,894 B2 * | 9/2025 | Marshall | A61B 17/1615 |
| 2012/0078258 A1 | 3/2012 | Lo et al. | |
| 2012/0143267 A1 | 6/2012 | Lannotti et al. | |
| 2015/0190151 A1 | 7/2015 | Budhabhatti et al. | |
| 2017/0150978 A1 | 6/2017 | Iannotti et al. | |
| 2019/0175277 A1 | 6/2019 | Chav et al. | |
| 2019/0254681 A1 | 8/2019 | Couture et al. | |
| 2020/0330161 A1 | 10/2020 | Chaoui et al. | |
| 2020/0390452 A1 | 12/2020 | Bojarski et al. | |
| 2020/0390501 A1 | 12/2020 | Brown et al. | |
| 2020/0405330 A1 | 12/2020 | Bonin, Jr. et al. | |
| 2021/0030428 A1 | 2/2021 | Rose et al. | |
| 2021/0030429 A1 | 2/2021 | Rose et al. | |
| 2021/0059693 A1 | 3/2021 | White et al. | |
| 2021/0059694 A1 | 3/2021 | White et al. | |
| 2021/0068844 A1 | 3/2021 | Lo et al. | |
| 2021/0085400 A1 | 3/2021 | Walch | |
| 2021/0128179 A1 | 5/2021 | Dupuis et al. | |
| 2021/0196290 A1 | 7/2021 | Iannotti et al. | |
| 2021/0220151 A1 | 7/2021 | Deransart et al. | |
| 2021/0251664 A1 | 8/2021 | Skelton | |
| 2021/0259844 A1 | 8/2021 | Penninger et al. | |
| 2021/0275227 A1 | 9/2021 | Park et al. | |
| 2021/0307796 A1 | 10/2021 | Marien et al. | |
| 2021/0322034 A1 | 10/2021 | Athwal et al. | |
| 2021/0386435 A1 | 12/2021 | Buza et al. | |
| 2022/0022895 A1 | 1/2022 | Neichel et al. | |
| 2022/0031475 A1 | 2/2022 | Deransart et al. | |
| 2022/0087827 A1 | 3/2022 | Bojarski et al. | |
| 2022/0110644 A1 | 4/2022 | Gargac et al. | |
| 2022/0151712 A1 | 5/2022 | Hughes et al. | |
| 2022/0160376 A1 | 5/2022 | Neichel et al. | |
| 2022/0257321 A1 | 8/2022 | Kehres et al. | |
| 2022/0265286 A1 | 8/2022 | Larche et al. | |
| 2022/0273370 A1 | 9/2022 | Fritzinger | |
| 2022/0330957 A1 | 10/2022 | Neichel et al. | |
| 2022/0338933 A1 | 10/2022 | Metcalfe et al. | |
| 2023/0061695 A1 | 3/2023 | Couture et al. | |
| 2023/0109478 A1 | 4/2023 | Chaoui et al. | |

OTHER PUBLICATIONS

International Search Report and Written Opinion for International Application No. PCT/US2025/028832 mailed Dec. 12, 2025.

* cited by examiner

PATIENT-SPECIFIC ORTHOPAEDIC TRANSFER GUIDES AND ASSOCIATED METHODS OF REPAIR

CROSS-REFERENCE TO RELATED APPLICATIONS

This application claims the benefit of U.S. Provisional Application No. 63/651,530, which was filed on May 24, 2024 and is incorporated herein by reference in its entirety.

BACKGROUND

This disclosure relates to surgical systems and methods for planning and implementing surgical procedures, including guides useful for implant placement.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to fill a defect in the glenoid bone. The implant may include a central post insertable in a recess of the glenoid to secure the implant to the glenoid. The implant may also be secured to the glenoid utilizing one or more fasteners.

SUMMARY

This disclosure relates to systems, devices and methods of performing a surgical procedure. The systems may be utilized for positioning one or more orthopaedic implants relative to the anatomy of a patient.

A system for an orthopaedic procedure may include a bushing having a bushing passage that may be dimensioned to receive a first guide element for guiding a surgical instrument. A locating component may include a main body having a locating passageway extending along a guide axis. The locating passageway may be dimensioned to at least partially receive the bushing to set a trajectory of the bushing passage. The locating component may include locating arms extending from the main body. The locating arms may include respective patient-specific contact surfaces that may be dimensioned to follow a bone contour. The locating component may include at least one extension that may extend circumferentially from a respective one of the locating arms relative to the guide axis. The at least one extension may include a guide passage that may be dimensioned to receive a second guide element. A position of the guide passage in the at least one extension may be based on a position of an implant passage of an implant that may be associated with a surgical plan.

A system for an orthopaedic procedure may include a locating component having a main body, a plurality of locating arms that may extending from a periphery of the main body, and a locating passageway in the main body. The locating arms may include respective patient-specific contact surfaces that may be dimensioned to follow a bone contour of a patient. A sleeve may be releasably securable to the locating component. The sleeve may include a sleeve passageway. A bushing may include a bushing passage that may be dimensioned to receive a first guide element for guiding a surgical instrument. The bushing may be at least partially insertable through the sleeve passageway and the locating passageway to set a trajectory of the bushing passage. A depth stop may be established by the locating component within the sleeve passageway. The depth stop may be dimensioned to limit insertion of a surgical tool through the locating passageway.

A method of performing an orthopaedic procedure may include positioning an orthopaedic guide on an articular surface of a bone. The guide may include a patient-specific locating component, a sleeve releasably secured to the locating component and a bushing inserted in the sleeve and the locating component. The method may include positioning a first guide element through the bushing and into the articular surface. The method may include positioning a second guide element through the locating component and into the articular surface. The method may include removing the bushing from the locating component without removing the first guide element from the bone. The method may include guiding a tool along the first guide element to form a recess in the articular surface. The method may include removing the locating component and the sleeve without removing the second guide element from the bone. The method may include at least partially inserting a fixation member of an implant into the recess. The method may include positioning a patient-specific surface of the implant on the articular surface by translating the implant along the second guide element.

A method of forming an orthopaedic guide may include defining, in a surgical plan for a patient, a position of an implant relative to an articular surface of a bone. The implant may include an implant body having at least one implant passage and at least one fixation member extending from the implant body. The fixation member may be dimensioned to secure the implant to the bone. The method may include defining, in the surgical plan, a position of a first guide element along the articular surface based on the defined position of the implant such that an axis of the first guide element may be aligned with a position associated with the fixation member. The method may include defining, in the surgical plan, a position of a second guide element along the articular surface based on the defined position of the implant such that an axis of the second guide element may be aligned with a position associated with the respective at least one implant passage. The method may include dimensioning a locating component including a main body. A plurality of locating arms may extend outwardly from the main body and may include patient-specific contact surfaces that may follow a contour of the articular surface. A locating passageway through the main body may establish the position of the first guide element when the contact surfaces may be seated on the articular surface of the bone. At least one extension may be swept along an arc path from a respective one of the locating arms such that a guide passage along the arc path may establish the position of the second guide element when the contact surfaces may be seated on the articular surface of the bone. The method may include generating a configuration associated with a physical instance of the locating component.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
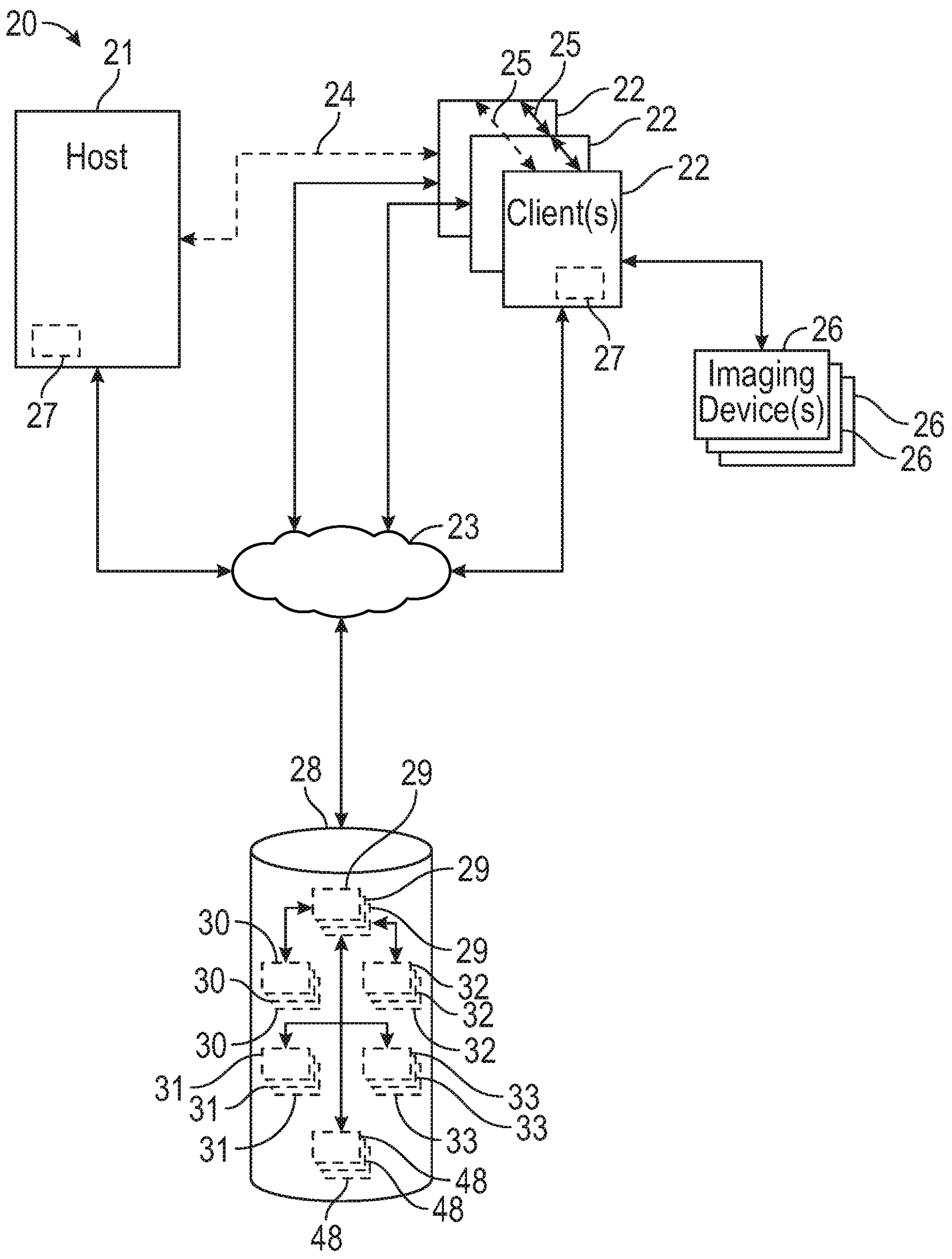
FIG. 1 discloses a planning system.

This disclosure relates to surgical systems, devices and methods for planning and implementing surgical procedures utilizing one or more implants and surgical guides.

The surgical systems and associated methods disclosed herein may be utilized to perform an arthroplasty for restoring functionality to various bones and joints, including any of the bones and associated joints disclosed herein such as shoulder, ankle, hip, knee and elbow joints. The surgical systems may be useful in positioning a patient-specific implant in a preselected position on the bone, which may be specified preoperatively in a surgical plan. The surgical systems may include a surgical (e.g., transfer) guide. The disclosed transfer guides may be used for the implantation of patient-specific and/or non-patient specific implants for treating a patient.

The disclosed guides and associated techniques may be utilized for shoulder arthroplasty to position an implant along an articular surface of a bone, such as a scapula. In implementations, the surface may be associated with a glenoid of the scapula. The guide may be patient-specific and may include a locating component, a sleeve and/or a bushing. The locating component may be patient-specific. The sleeve and/or bushing may be reusable. The locating component may include a guide (e.g., main) body and one or more (e.g., integrally formed) locating arms that may extend outwardly from the guide body. The locating arms may include respective contact surfaces which may have a patient-specific contour. The patient-specific contour may be complementary to a profile of an (e.g., articular) surface of the bone such that the locating component may only be fully seated in a single patient-specific position relative to the bone. The contoured contact surfaces may not be contiguous with each other.

At least some of the locating arms may include overhangs, but some may not. The overhangs may be dimensioned to overhang respective portions of the rim of the socket of a joint, such as the glenoid. Each of the locating arms may include an engagement face dimensioned to rest on the glenoid rim. Contact surfaces of the overhangs and the engagement faces may not be patient-specific.

The guide body of the locating component may include a locating passageway that may be dimensioned to accommodate a (e.g., distal) portion of the bushing. The sleeve may have a sleeve passageway that may be aligned with the locating passageway of the guide body. The sleeve passageway may be dimensioned to receive a (e.g., intermediate) portion of the bushing. The locating passageway may be dimensioned to receive a (e.g., proximal) portion of the bushing. The bushing may include at least one guide bore (e.g., bushing passage) dimensioned to establish a trajectory of a guide element (e.g., pin) relative to the bone. After the guide pin is properly located, the bushing may be removed. A cannulated drill bit may be positioned in the passageway and over the guide pin for making a hole in the bone to receive an implant post.

The patient-specific locating component may include one or more guide passages. The guide passages may be dimensioned to receive respective guide elements (e.g., guide pins) for orienting the implant relative to the bone. The guide passages may be spaced circumferentially from the locating arms relative to an axis of the guide body. Each guide passage may be disposed in its own extension, which may be dimensioned to extend from a sidewall of the locating arm.

The distal surfaces of the locating component that define openings of the locating passageway and guide passages may be spaced apart from the bone when the locating component is seated on the bone. The distal surfaces may not have a patient-specific contour.

The locating component, sleeve and bushing may be made of various metallic and/or non-metallic materials, including any of the materials disclosed herein. The locating component, sleeve and bushing may be made of the same metallic material, but they may be made of different metallic materials.

Techniques for performing a shoulder arthroplasty using the disclosed transfer guides are disclosed. The surgeon may select an implant for treating a patient. The implant may be patient-specific or non-patient specific. In implementations, the surgeon may expose a glenoid of the patient. A surgeon may place the locating component on the glenoid face in a fully seated position with the patient-specific contour of the contact surfaces on the locating arms engaging the surface contour of the glenoid. The surgeon may drive a first guide element (e.g., guide pin) through one of the guide passages. The surgeon may remove the guide from the glenoid and check (e.g., verify) a fit of the implant by inserting a trial implant over the secondary pin and into the glenoid. If the surgeon is dissatisfied with the fit, the surgeon may remove the first guide pin and position a guide element (e.g., guide pin) in another one of the guide passages and then may recheck the fit with the trial implant. The surgeon may drive a second guide element (e.g., guide pin) through the guide bore of the bushing and into the glenoid. The bushing may be situated in the passageway of the locating component. The surgeon may remove the guide from the glenoid and may check (e.g., verify) the implant fit by inserting the trial implant over the first and second guide elements and onto the glenoid. The surgeon may reposition the guide on the glenoid with the bushing removed. The surgeon may translate a cannulated drill bit along the second guide element and into contact with the glenoid and may drill a recess (e.g., hole) in the glenoid. After removing the drill bit and guide, the surgeon may place the implant on the glenoid. The surgeon may couple an inserter to the implant. The surgeon may translate the inserter and implant together along the first and/or second guide elements. The surgeon may impact the inserter to seat the implant on the glenoid and impact fixation element(s) (e.g., post) of the implant in the prepared recess. The surgeon may secure the implant to the glenoid with one or more fasteners (e.g., compression screws).

A system for an orthopaedic procedure may include a bushing having a bushing passage that may be dimensioned to receive a first guide element for guiding a surgical instrument. A locating component may include a main body having a locating passageway extending along a guide axis. The locating passageway may be dimensioned to at least partially receive the bushing to set a trajectory of the bushing passage. The locating component may include locating arms extending from the main body. The locating arms may include respective patient-specific contact surfaces that may be dimensioned to follow a bone contour. The locating component may include at least one extension that may extend circumferentially from a respective one of the locating arms relative to the guide axis. The at least one extension may include a guide passage that may be dimensioned to receive a second guide element. A position of the guide passage in the at least one extension may be based on a position of an implant passage of an implant that may be associated with a surgical plan.

In any implementations, the implant may be patient-specific.

In any implementations, the system may include an impactor adapted to position an implant relative to bone. The impactor may include an impactor body having an impactor passage. The impactor may be dimensioned such that the impactor passage may be substantially aligned with the implant passage in an assembled configuration.

In any implementations, the at least one extension may be dimensioned to follow an arc path about the guide axis. The position of the guide passage may be established along the arc path.

In any implementations, the at least one extension may include a plurality of extensions. The arc paths of the respective extensions may have a common radius.

In any implementations, positions of the respective locating arms relative to the main body may be set prior to the positions of the guide passages in the extensions.

In any implementations, the bushing passage and the at least one guide passage may extend along respective passage axes. The passage axes may be substantially parallel to each other in an assembled configuration.

In any implementations, the system may include a sleeve having a sleeve passageway. The sleeve may be releasably securable to a proximal portion of the main body. The sleeve passageway and the locating passageway may be at least partially aligned with each other in an assembled configuration. The bushing may be at least partially insertable through the sleeve passageway and the locating passageway in an assembled configuration to set the trajectory of the bushing passage.

In any implementations, at least one overhang may extend from an end portion of a respective one of the locating arms. The at least one overhang may be dimensioned to contact a non-articular surface of a bone to limit movement of the locating component when the contact surfaces may be seated on an articular surface of a bone associated with the bone contour.

In any implementations, the at least one extension may be cantilevered from the respective locating arm.

In any implementations, the at least one extension may have an arcuate geometry dimensioned to follow a circumferential path about the guide axis.

In any implementations, the locating component may be monolithic.

A system for an orthopaedic procedure may include a locating component having a main body, a plurality of locating arms that may extending from a periphery of the main body, and a locating passageway in the main body. The locating arms may include respective patient-specific contact surfaces that may be dimensioned to follow a bone contour of a patient. A sleeve may be releasably securable to the locating component. The sleeve may include a sleeve passageway. A bushing may include a bushing passage that may be dimensioned to receive a first guide element for guiding a surgical instrument. The bushing may be at least partially insertable through the sleeve passageway and the locating passageway to set a trajectory of the bushing passage. A depth stop may be established by the locating component within the sleeve passageway. The depth stop may be dimensioned to limit insertion of a surgical tool through the locating passageway.

In any implementations, the surgical tool may be slidably receivable through the sleeve passageway such that an abutment of the surgical tool may engage the depth stop to limit insertion of the surgical tool through the locating passageway.

In any implementations, the surgical instrument may be a drill.

In any implementations, a twist-lock mechanism may be adapted to releasably secure the sleeve and the locating component to each other.

In any implementations, the twist-lock mechanism may include a push-lock adapted to selectively lock the locating component and sleeve together.

In any implementations, the bushing may include a first type of material. The locating component may include a second type of material that may differ from the first type of material.

In any implementations, the main body of the locating component may have a tubular geometry.

In any implementations, the locating component may be monolithic.

A method of performing an orthopaedic procedure may include positioning an orthopaedic guide on an articular surface of a bone. The guide may include a patient-specific locating component, a sleeve releasably secured to the locating component and a bushing inserted in the sleeve and the locating component. The method may include positioning a first guide element through the bushing and into the articular surface. The method may include positioning a second guide element through the locating component and into the articular surface. The method may include removing the bushing from the locating component without removing the first guide element from the bone. The method may include guiding a tool along the first guide element to form a recess in the articular surface. The method may include removing the locating component and the sleeve without removing the second guide element from the bone. The method may include at least partially inserting a fixation member of an implant into the recess. The method may include positioning a patient-specific surface of the implant on the articular surface by translating the implant along the second guide element.

In any implementations, the step of positioning the guide may include inserting the bushing at least partially through a sleeve passage in the sleeve and a locating passageway in the locating component such that the bushing may be situated above the locating component relative to the articular surface.

In any implementations, the locating component may include a main body and a plurality of locating arms that may extend from a periphery of the main body. The locating arms may have respective patient-specific contact surfaces that may be dimensioned to follow a contour of the articular surface. The step of positioning the guide may include positioning the contact surfaces in abutment with the articular surface to establish a patient-specific position of the locating component.

In any implementations, the contact surfaces may be discrete.

In any implementations, the locating component may include at least one overhang that may extend from an end portion of a respective one of the locating arms. The method may include positioning the at least one overhang in engagement with a rim of the bone to set a position of the locating component on the articular surface.

In any implementations, the at least one overhang may include a plurality of overhangs that may be circumferentially distributed about the main body. The overhangs may be dimensioned such that the locating component may be removable from the articular surface without removing the first and second guide elements from the bone.

In any implementations, the patient-specific contact surfaces may be dimensioned to terminate prior to the respective overhangs.

In any implementations, the step of positioning the second guide element may include inserting the second guide element through a guide passage in an extension from the respective locating arm. A position of the guide passage may be set along an arc path of the extension. The arc path may be dimensioned to extend about a guide axis of the locating component.

In any implementations, the position of the guide passage may be set along the arc path subsequent to a circumferential position of the respective locating arm being set relative to the guide axis.

In any implementations, the implant may include a plurality of implant passages. The locating component may include a plurality of extensions that may extend circumferentially from one or more of locating arms relative to a guide axis of the locating component. Each of the extensions may include a respective guide passage that may be associated with a position of a respective one of the implant passages. The step of positioning the implant may include inserting the second guide element through a selected one of the implant passages and then into the articular surface to limit relative movement between the implant and the bone.

In any implementations, the guide passages may be circumferentially offset at different distances from the respective locating arms relative to the guide axis based on the circumferential positions of the implant passages relative to an implant axis of the implant.

In any implementations, the step of positioning the implant may include translating the implant and an impactor along the second guide element and then impacting, using the impactor, the fixation member of the implant into the recess.

In any implementations, the step of guiding the tool may include moving an abutment of the tool into engagement with a depth stop to limit translation of the tool along the first guide element.

In any implementations, the method may include checking a fit of the patient-specific surface of the implant on the articular surface by removing the guide from the articular surface and then translating a trial implant along at least one of the first and second guide elements such that a patient-specific surface of the trial implant may abut the articular surface.

In any implementations, the method may include securing the implant to the bone with one or more fasteners.

In any implementations, the articular surface may be associated with a glenoid of the patient.

In any implementations, the tool may be a drill.

A method of forming an orthopaedic guide may include defining, in a surgical plan for a patient, a position of an implant relative to an articular surface of a bone. The implant may include an implant body having at least one implant passage and at least one fixation member extending from the implant body. The fixation member may be dimensioned to secure the implant to the bone. The method may include defining, in the surgical plan, a position of a first guide element along the articular surface based on the defined position of the implant such that an axis of the first guide element may be aligned with a position associated with the fixation member. The method may include defining, in the surgical plan, a position of a second guide element along the articular surface based on the defined position of the implant such that an axis of the second guide element may be aligned with a position associated with the respective at least one implant passage. The method may include dimensioning a locating component including a main body. A plurality of locating arms may extend outwardly from the main body and may include patient-specific contact surfaces that may follow a contour of the articular surface. A locating passageway through the main body may establish the position of the first guide element when the contact surfaces may be seated on the articular surface of the bone. At least one extension may be swept along an arc path from a respective one of the locating arms such that a guide passage along the arc path may establish the position of the second guide element when the contact surfaces may be seated on the articular surface of the bone. The method may include generating a configuration associated with a physical instance of the locating component.

In any implementations, the locating passageway may be dimensioned to slidably receive a bushing such that a bushing passageway of the bushing may establish the position of the first guide element when the contact surfaces may be seated on the articular surface of the bone.

In any implementations, the locating passageway may be dimensioned to at least partially receive a tool. The main body may be dimensioned to establish a depth stop that may limit translation of the tool along the axis of the first guide element for forming a recess in the articular surface of the bone that may at least partially receive the fixation member.

In any implementations, the tool may be a drill.

In any implementations, the at least one extension may include a plurality of extensions. The arc paths of the respective extensions may have a common radius associated with an axis of the implant.

In any implementations, the implant may include one or more fixation apertures that may be dimensioned to receive respective fasteners for securing the implant to bone. The at least one implant passage may be spaced apart from all of the one or more fixation apertures.

FIG. 1 discloses a planning system 20 that may be utilized for planning surgical procedures. The system 20 may be used for planning orthopaedic procedures, including pre-operatively, intra-operatively and/or post-operatively to create, edit, execute and/or review surgical plans. The system 20 may be utilized for various orthopaedic and other surgical procedures, such as an arthroplasty to repair a joint. The system 20 may be utilized in the design and/or placement of implant(s) and/or surgical (e.g., transfer) guides, such as an implant incorporated into a shoulder prosthesis or a transfer guide for positioning one or more surgical instruments and/or implants. Although the planning systems and methods disclosed herein primarily refer to repair of a glenoid during an anatomic or reverse shoulder reconstruction, it should be understood that the planning system 20 may be utilized in the repair of other locations of the anatomy and other surgical procedures including repair of other bones and joints such as the humerus, wrist, hand, hip, knee or ankle.

The system 20 may include a host computer 21 and one or more client computers 22. The host computer 21 may be configured to execute one or more software programs. In implementations, the host computer 21 may be more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network.

The host computer 21 and each client computer 22 may include one or more computer processors, memory, storage means, network devices, and input and/or output devices and/or interfaces. The input devices may include a keyboard, mouse, etc. The output device may include a monitor, speakers, printers, etc. The memory may include UVPROM, EEPROM, FLASH, RAM, ROM, DVD, CD, a hard drive, or other computer readable medium which may store data and/or other information relating to the planning and implementation techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. In another implementation, the client computers 22 may be configured to communicate with each other directly via a peer-to-peer interface 25.

The system 20 may include, or may be coupled to, one or more imaging devices 26. Each client computer 22 may be coupled to one or more imaging devices 26. Each imaging device 26 may be configured to capture or acquire one or more images 30 of patient anatomy residing within a scan field (e.g., window) of the imaging device 26. The imaging device 26 may be configured to capture or acquire two-dimensional (2D) and/or three-dimensional (3D) greyscale and/or color images 30. Various imaging devices 26 may be utilized, such as an X-ray machine, computerized tomography (CT) machine or magnetic resonance imaging (MRI) machine that may obtain one or more images of a patient.

The client computers 22 may be configured to execute one or more software programs, including various surgical tools. Each client computer 22 may be operable to access and locally and/or remotely execute a planning environment 27. The planning environment 27 may be a standalone software package or may be incorporated into another surgical tool. The planning environment 27 may be configured to communicate with the host computer 21 either over the network 23 or directly through the direct client interface 24.

The planning environment 27 may be configured to interact with one or more of the imaging devices 26 to capture or acquire images 30 of patient anatomy. The planning environment 27 may provide a display or visualization of one or more images 30, virtual anatomical (e.g., bone) models 31, virtual implant models 32 and/or virtual surgical (e.g., transfer) guide models 48 via one or more graphical user interfaces (GUI). Each image 30, bone model 31, implant model 32, transfer model 48 and other data and information may be stored in one or more files or records according to a specified data structure.

The system 20 may include at least one storage system 28, which may be operable to store or otherwise provide data to other computing devices. The storage system 28 may be a storage area network device (SAN) configured to communicate with the host computer 21 and/or the client computers 22 over the network 23. In implementations, the storage system 28 may be incorporated within, or may be directly coupled to, the host computer 21 and/or client computers 22. The storage system 28 may be configured to store one or more of computer software instructions, data, database files, configuration information, etc.

In implementations, the system 20 may be a client-server architecture configured to execute computer software on the host computer 21, which may be accessible by the client computers 22 using either a thin client application or a web browser executing on the client computers 22. The host computer 21 may be operable to load the computer software instructions from local storage, or from the storage system 28, into memory and may execute the computer software using the one or more computer processors.

The system 20 may include one or more databases 29. The databases 29 may be stored at a central location, such as the storage system 28. In other implementations, one or more databases 29 may be stored at the host computer 21 and/or may be a distributed database provided by one or more of the client computers 22. Each database 29 may be a relational database configured to associate one or more images 30, bone models 31, implant models 32 and/or transfer models 48 to each other and/or a surgical plan 33. Each surgical plan 33 may be associated with the anatomy of a respective patient. Each image 30, bone model 31, implant model 32, transfer model 48 and/or surgical plan 33 may be assigned a unique identifier or database entry. The database 29 may be configured to store data and other information corresponding to the images 30, bone models 31, implant models 32, transfer models 48 and surgical plans 33 in one or more database records or entries, and/or may be configured to link or otherwise associate one or more files corresponding to each respective image 30, bone model 31, implant model 32, transfer model 48 and surgical plan 33. Images 30, bone models 31, implant models 32, transfer models 48 and associated surgical plans 33 stored in the database(s) 29 may correspond to respective patient anatomies from prior, planned and/or hypothetical surgical cases, and may be arranged into one or more predefined categories such as sex, age, ethnicity, defect category, procedure type, surgeon, facility or organization, etc.

Each image 30 and bone model 31 may include data and other information obtained from one or more medical devices or tools, such as the imaging devices 26. The bone model 31 may include coordinate information relating to an anatomy of the patient obtained or derived from image(s) 30 captured or otherwise obtained by the imaging device(s) 26. Each implant model 32 and transfer model 48 may include geometry and/or coordinate information associated with a predefined design or a design established or modified by the planning environment 27. The planning environment 27 may incorporate and/or interface with one or more modeling packages, such as a computer aided design (CAD) package, to render the models 31, 32, 48 as two-dimensional (2D) and/or three-dimensional (3D) volumes or constructs, which may overlay one or more of the images 30 in a display screen of a GUI.

The implant models 32 may correspond to implants and components of various configurations, shapes, sizes, procedures, instrumentation, etc. The implant model 32 may be associated with a patient-specific implant for treating a single patient or may be non-patient specific (e.g., generic) for treating different patients. Each implant may include, or may otherwise be associated with, one or more components that may be situated at a surgical site including plates, screws, anchors, nails, suture, grafts, etc. Each implant model 32 may correspond to a single component or may include two or more components that may be configured to establish an assembly. The implant models 32 may include base plates coupled to an articulation member, bone plates configured to interconnect adjacent bones or bone fragments, intermedullary nails, suture anchors, etc. The articulation member may have an articular surface dimensioned to mate with an articular surface of an opposed bone or implant. Each implant and associated component(s) may be formed of various materials, including metallic and/or non-metallic materials. Each bone model 31, implant model 32 and transfer model 48 may correspond to 2D and/or 3D geometry and may be utilized to generate a wireframe, mesh and/or solid construct in a display.

Each surgical plan 33 may be associated with one or more of the images 30, bone models 31, implant models 32 and/or transfer models 48. The surgical plan 33 may include various parameters associated with the images 30, bone models 31, implant models 32 and/or transfer models 48. The surgical plan 33 may include parameters relating to bone density and bone quality associated with patient anatomy captured in the image(s) 30. The surgical plan 33 may include parameters including spatial information relating to relative positioning and coordinate information of the selected bone model(s) 30, implant model(s) 32 and/or transfer model(s) 48.

The surgical plan 33 may include one or more revisions to a bone model 31 and information relating to a position of an implant model 32 and/or transfer model 48 relative to the original and/or revised bone model 31. The surgical plan 33 may include coordinate information relating to the revised bone model 31 and a relative position of the implant model 32 and/or transfer model 48 in predefined data structure(s). The planning environment 27 may be configured to make one or more revisions to a transfer model 48 automatically or in response to user interaction with the user interface. Revisions to each bone model 31, implant model 32, transfer model 48 and/or surgical plan 33 may be stored in the database 29 automatically and/or in response to user interaction with the system 20.

One or more surgeons and other users may be provided with a planning environment 27 via the client computers 22 and may simultaneously access each image 30, bone model 31, implant model 32, transfer model 48 and surgical plan 33 stored in the database(s) 29. Each user may interact with the planning environment 27 to create, view and/or modify various aspects of the surgical plan 33. Each client computer 22 may be configured to store local instances of the images 30, bone models 31, implant models 32, transfer models 48 and/or surgical plans 33, which may be synchronized in real-time or periodically with the database(s) 29. The planning environment 27 may be a standalone software package executed on a client computer 22 or may be provided as one or more services executed on the host computer 21.

Figure 2:
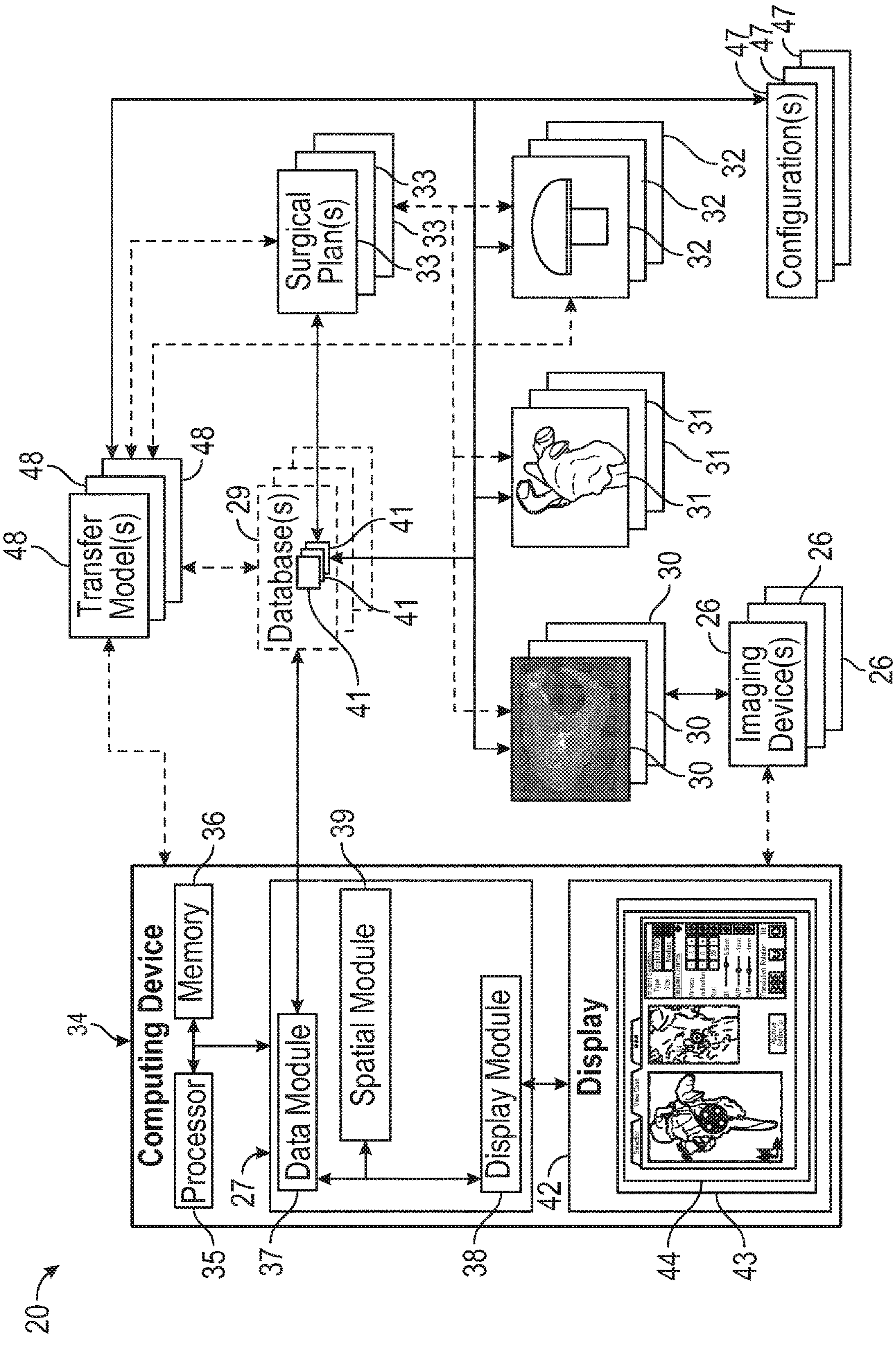
FIG. 2 discloses another planning system including a user interface.

Referring to FIG. 2, with continuing reference to FIG. 1, the system 20 may include a computing device 34 including one or more processors 35 coupled to memory 36. The computing device 34 may include any of the computing devices disclosed herein, including the host computer 21 and/or client computer 22. The processor(s) 35 may be configured to collectively execute a planning environment 27 for creating, editing, executing and/or reviewing one or more surgical plans 33 and any associated bone models 31, implant models 32 and transfer models 48 during pre-operative, intra-operative and/or post-operative phases of a surgery.

The planning environment 27 may include a data module 37, a display module 38 and a spatial module 39. Although three modules are disclosed, it should be understood that fewer or more than three modules may be utilized and/or one or more of the modules may be combined to provide the disclosed functionality.

The data module 37 may be configured to access, retrieve and/or store data and other information in the database(s) 29 corresponding to one or more images 30 of patient anatomy, bone model(s) 31, implant model(s) 32, transfer model(s) 48 and/or surgical plan(s) 33. The data and other information may be stored in one or more databases 29 as one or more records or entries 41. In implementations, the data and other information may be stored in one or more files that may be accessible by referencing one or more objects or memory locations referenced by the records 41.

The memory 36 may be configured to access, load, edit and/or store instances of one or more images 30, bone models 31, implant models 32, transfer models 48 and/or surgical plans 33 in response to one or more commands from the data module 37. The data module 37 may be configured to access a virtual bone model 31 from memory, such as the memory 36 and/or storage system 28. The bone model 31 may be associated with a bone and/or joint of a patient. The data module 37 may be configured to cause the memory 36 to store a local instance of the image(s) 30, bone model(s) 31, implant model(s) 32, transfer model(s) 48 and/or surgical plan(s) 33, which may be synchronized with the records 41 in the database(s) 29.

The data module 37 may be configured to receive data and other information corresponding to at least one or more images 30 of patient anatomy from various sources such as the imaging device(s) 26. The data module 37 may be configured to command the imaging device 26 to capture or otherwise acquire the images 30 automatically or in response to user interaction.

The display module 38 may be configured to display data and other information relating to one or more surgical plans 33 in at least one graphical user interface (GUI) 43, including one or more of the images 30, bone models 31, implant models 32 and/or transfer models 48. The computing device 34 may incorporate, or may be coupled to, a display device 42. The user interface 43 may include one or more display windows 44. The display module 38 may be configured to cause the display device 42 to display information in the display window(s) 44 and/or another portion of the user interface 43. A surgeon or other user may interact with the user interface 43 via the planning environment 27 to view one or more images 30 of patient anatomy and/or any associated bone models 31, implant models 32 and transfer models 48. The surgeon or other user may interact with the user interface 43 via the planning environment 27 to create, edit, execute and/or review one or more surgical plans 33.

The planning system 20 may be configured to access, generate, review, edit and/or approve one or more configurations 47 associated with respective physical implant(s) and/or surgical (e.g., transfer) guide(s), including any of the implants and transfer guides disclosed herein. The virtual implant model 32 may be representative of a respective physical implant. The virtual transfer model 48 may be representative of a respective physical transfer guide. The configuration 47 may specify various information for forming an instance of a respective physical implant or transfer guide, which may be based on a respective virtual implant model 32 or transfer model 48. Each configuration 47 may include one or more files in a predetermined data structure or format. In implementations, the configuration 47 may include a coordinate set and/or other information such as material selection(s) associated with volume(s) of the physical implant or transfer guide. The physical implant(s) and transfer guide(s) may be formed utilizing various techniques, including any of the techniques disclosed herein such as rapid prototyping (e.g., printing) and other additive manufacturing techniques, casting, machining, etc.

Referring to FIGS. 3A-3E, with continuing reference to FIG. 2, an orthopaedic implant 50 according to an implementation is disclosed. The implant 50 may be a physical implant or may be an implant model 32 associated with a physical implant. The implant 50 may be configured to abut or contact bone or other tissue. The bone may be a portion of a glenoid or another bone associated with a joint of a patient, including any of the bones and joints disclosed herein. In implementations, the implant 50 may be utilized in an anatomical and/or reverse shoulder reconstruction. The bone may be associated with a respective bone model 31.

Figure 10:
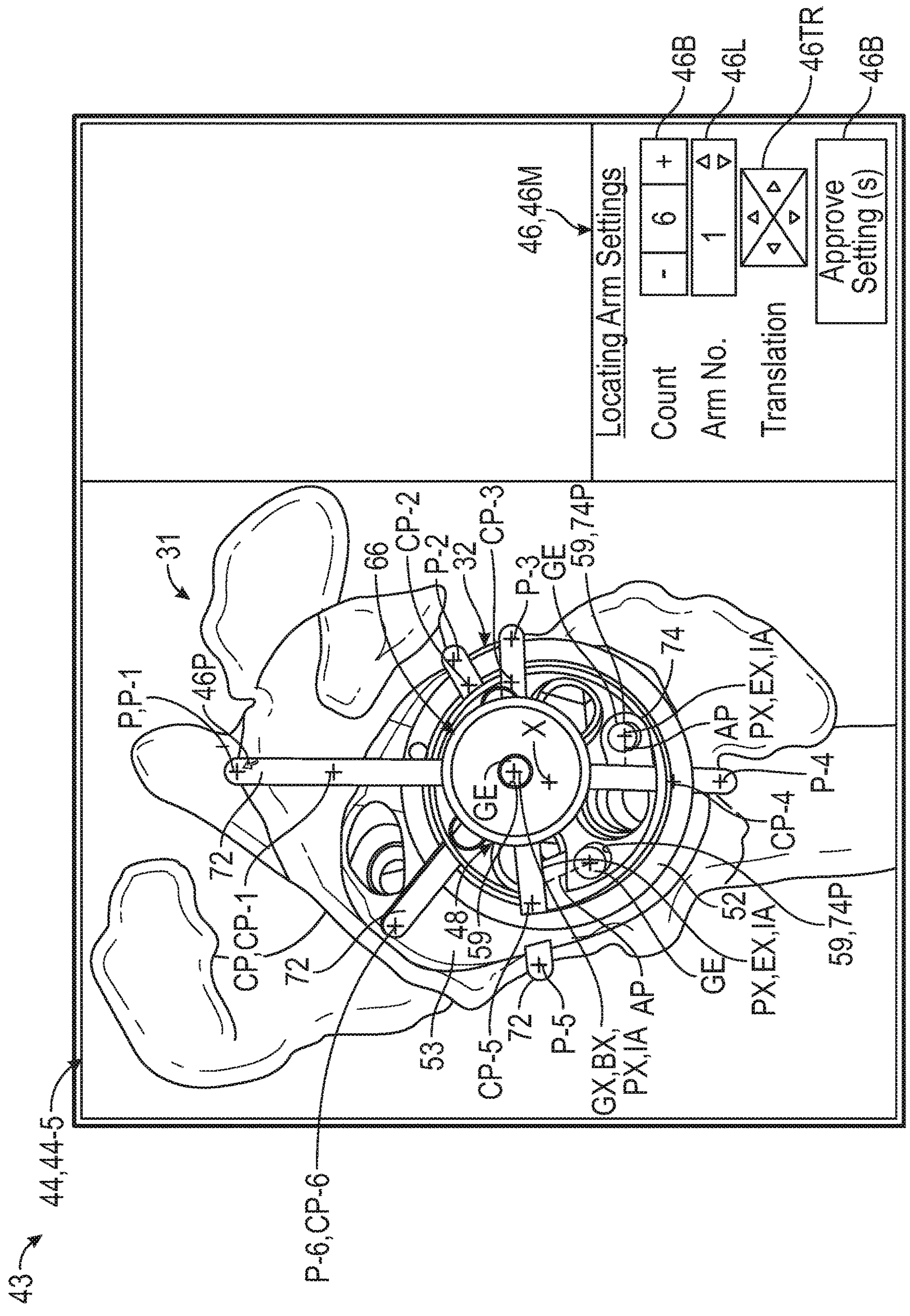
FIG. 10 discloses a transfer model relative to the implant model of FIG. 8 in a display window of the user interface of FIG. 2.

The implant 50 may be positioned on the anatomy using a surgical (e.g., transfer) guide, including any of the transfer guides disclosed herein. The surgeon may position and orient the implant 50 relative to a bone using one or more guide elements, which may be positioned in the bone using the transfer guide. In the implementation of FIG. 10, the transfer guide may be associated with a respective transfer model 48. The transfer model 48 may be dimensioned to at least partially receive or otherwise interface with one or more guide elements GE, which may be insertable in bone or other tissue at the surgical site The transfer model 48 may be dimensioned to establish a position and/or orientation of the guide element(s) GE and an associated implant 50 relative to the bone according to a surgical plan 33. The planning environment 27 may be configured to establish a geometry of the transfer model 48 based on a position and orientation of the guide element(s) GE and a geometry of the associated implant model 32 for implementing the surgical plan 33.

Figure 3A:
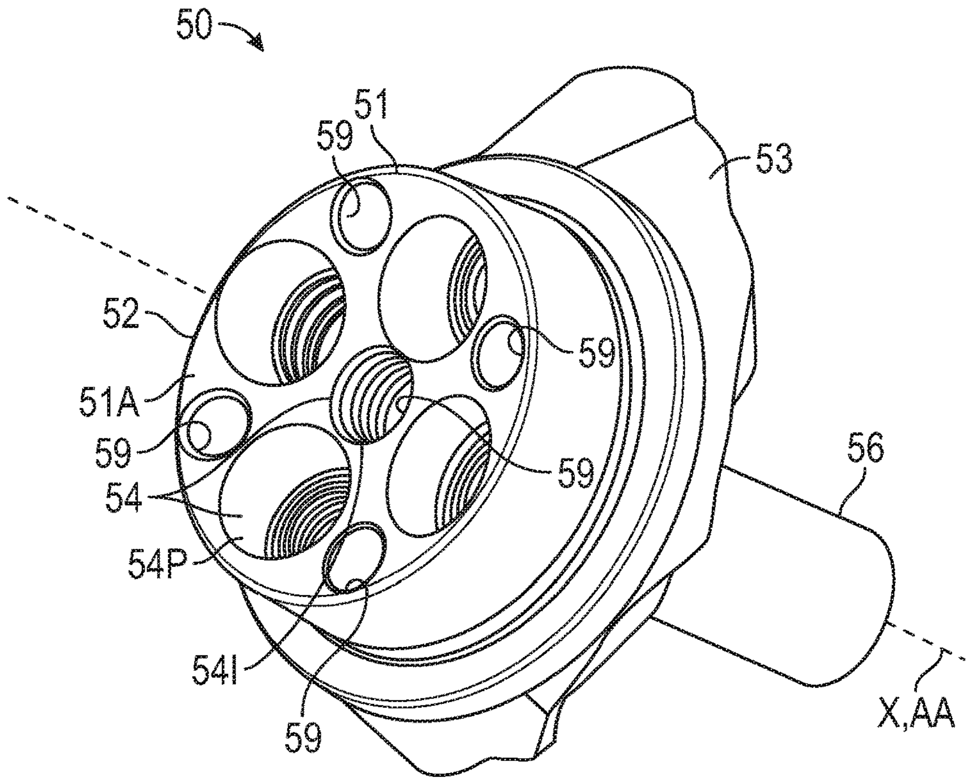
FIGS. 3A-3E disclose an orthopaedic implant.
Figure 3B:
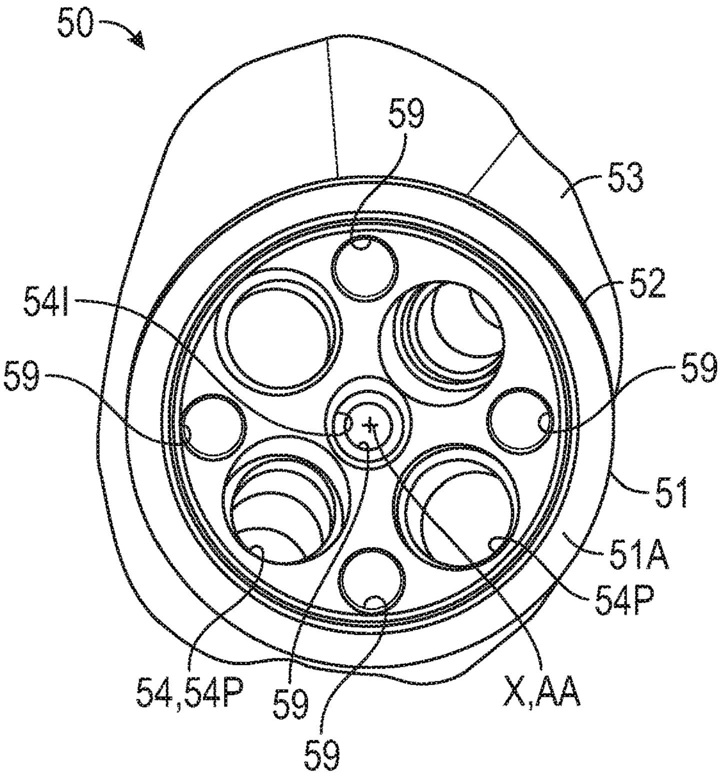
Figure 3C:
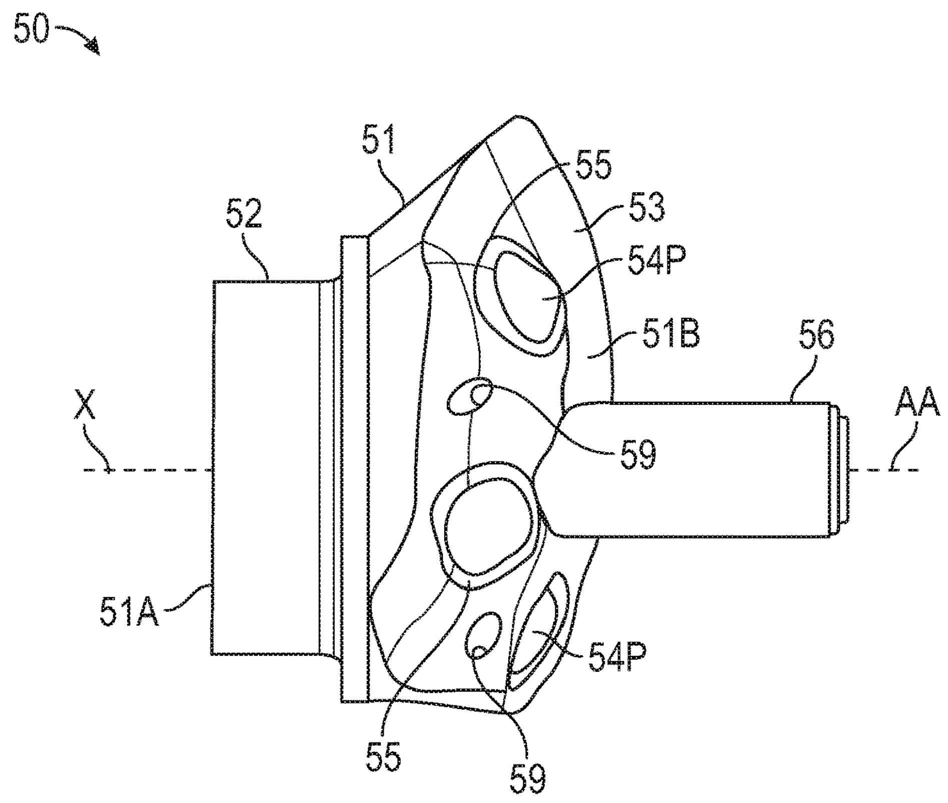
Figure 3D:
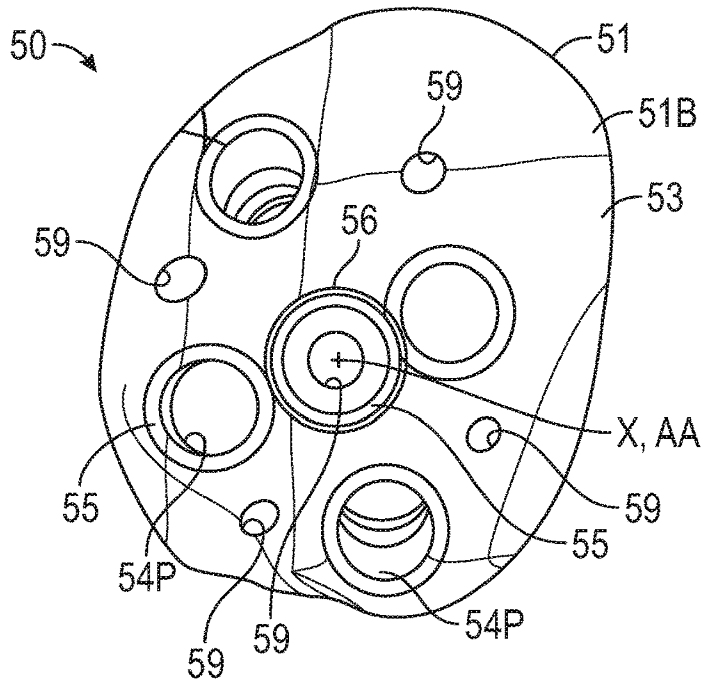
Figure 3E:
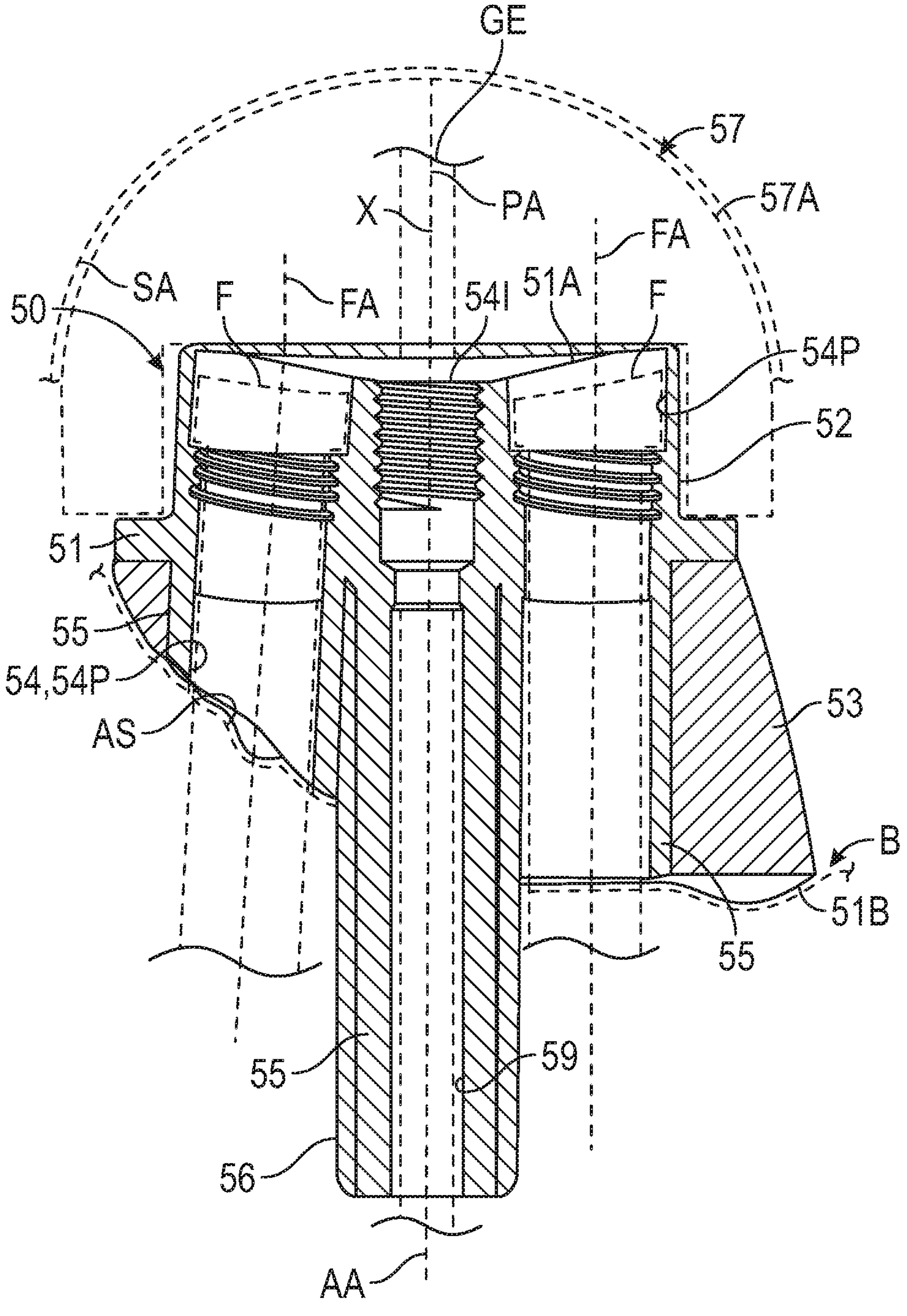

The implant 50 may include a main body 51 dimensioned to abut bone at a surgical site (e.g., bone B of FIG. 3E). The main body 51 may extend along an implant (e.g., longitudinal) axis X between a first (e.g., front) face 51A and a second (e.g., rear) face 51B generally opposed to the first face 51A. The rear face 51B may be dimensioned to contact bone or other tissue to seat the implant 50 at the surgical site.

In the implementation of FIG. 3E, the main body 51 may be dimensioned to receive one or more fasteners F (shown in dashed lines). Each of the fasteners F may be dimensioned to be at least partially received in bone to secure the implant 50 at the surgical site. Various fasteners may be utilized with the implant 50, such as compression screws, nails, pins, etc., suitable for securing the implant 50.

The implant 50 may include a baseplate 52 and/or augment 53 that may establish the main body 51. The augment 53 may extend outwardly from the baseplate 52 relative to the axis X. The baseplate 52 may establish the front face 51A of the main body 51. The augment 53 may establish the rear face 51B of the main body 51. The baseplate 52 and augment 53 may be integrally formed to establish a monolithic or unitary component or may be separate and distinct components that may be fixedly attached or otherwise secured to each other. The baseplate 52 and augment 53 may be formed utilizing various techniques, such as casting or additive manufacturing. In implementations, the augment 53 may be omitted.

The baseplate 52 and augment 53 may have various geometries. A perimeter of the baseplate 52 and/or another portion of the main body 51 may have a substantially circular or elliptical geometry, although other geometries may be utilized. For the purposes of this disclosure, the terms "substantially," "approximately" and "about" mean ±10 percent of the stated value or relationship unless otherwise indicated. The augment 53 may be dimensioned to contact bone. The rear face 51B and/or other portions of the main body 51 may be dimensioned to approximate a geometry of a bone defect or may have one or more surfaces having a patient-specific geometry dimensioned to substantially conform to or otherwise follow a surface contour of the bone associated with a respective patient. The surface contour may be established along an articular surface of the respective bone. The rear face 51B of the implant 50 may be dimensioned to substantially follow a surface contour of a bone (e.g., bone B of FIG. 3E). In implementations, the planning environment 27 may be configured to define a geometry of a virtual implant model 32 associated with the implant 50 such that the rear face 51B may have a patient-specific contour dimensioned to substantially follow a contour of an articular surface AS associated with the virtual bone model 31 (shown in dashed lines in FIG. 3E). In other implementations, the rear face 51B of the implant 50 may include one or more regions having a substantially planar or other non-patient specific geometry.

The implant 50 may include one or more (e.g., fixation) apertures 54 for securing the implant 50 at the surgical site. The apertures 54 may extend through the main body 51 of the implant 50, including the baseplate 52 and/or augment 53. The apertures 54 may be passages that may extend between the front face 51A and rear face 51B of the implant 50. In implementations, the apertures 54 may include an intermediate (e.g., central) aperture 541 and/or one or more peripheral apertures 54P. The peripheral apertures 54P may be circumferentially distributed about the implant axis X (e.g., FIG. 3B). In the implementation of FIG. 3E, one or more of the apertures 54 may be dimensioned to receive a respective fastener F to secure the implant 50 to bone or other tissue at the surgical site. Each fastener F may extend along a respective fastener axis FA. The planning environment 27 may be configured to establish a trajectory of each fastener axis FA and respective aperture 54 of the associated implant model 32.

The implant 50 may include one or more (e.g., implant or positioning) passages 59 for positioning the implant 50 at the surgical site. In implementations, one or more fixation apertures 54 may be at least partially aligned with respective implant passage 59. The passages 59 may extend through the main body 51 of the implant 50, including the baseplate 52 and/or augment 53. The passages 59 may be dimensioned to receive an instrument or other surgical device. The instrument may include a guide element GE such as a Kirschner wire or Steinman pin for positioning the implant 50 at the surgical site (e.g., guide elements GE of FIGS. 3E and 10). The planning environment 27 may be configured to establish a trajectory of the respective guide element(s) GE. A physical surgical (e.g., transfer) guide associated with a transfer model 48 may be dimensioned to establish a position and/or orientation of the guide element(s) GE. The implant passages 59 may be established at various positions in the implant 50. In implementations, the intermediate aperture 541 may establish, or may be at least partially aligned with, one of the positioning passages 59. A set of passages 59 may be established about the intermediate aperture 541. The set of passages 59 may be interspersed with a set of the peripheral apertures 54P. In implementations, the implant passage(s) 59 may be spaced apart from all of the fixation apertures 54 of the implant 50.

The implant 50 may include one or more internal walls 55 that may establish the respective apertures 54. In implementations, the internal walls 55 may have a generally tubular geometry. The augment 53 may be substantially solid or may be porous.

Figure 4:
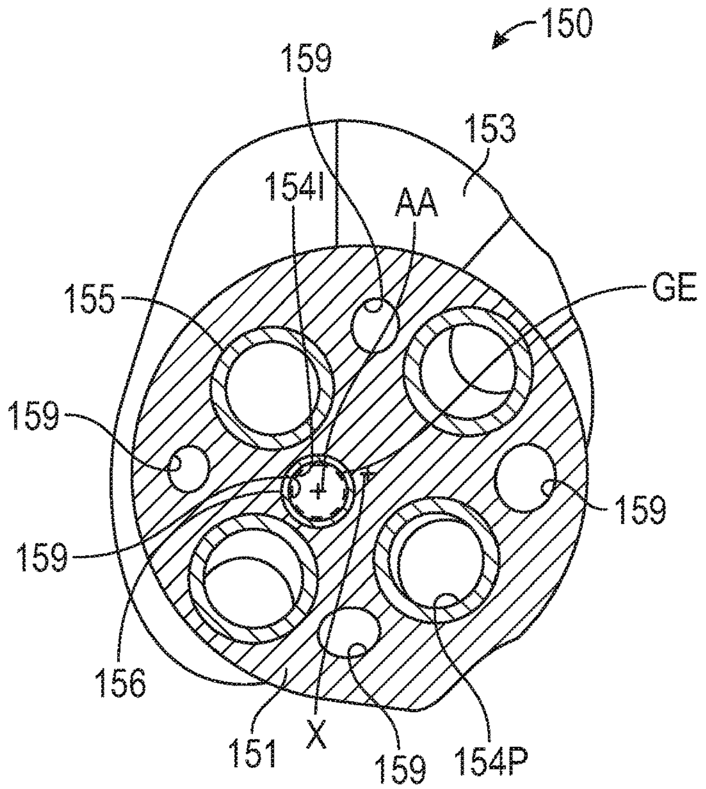
FIGS. 4-5 disclose sectional views of implementations of orthopaedic implants.
Figure 5:
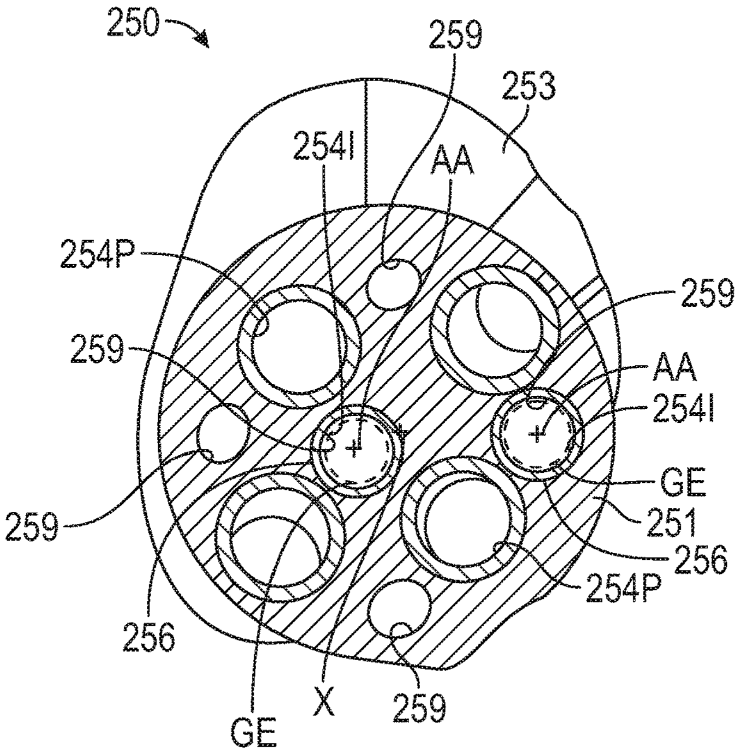

The implant 50 may include one or more fixation members 56. Each fixation member 56 may be dimensioned to secure the implant 50 to bone and/or other tissue at the surgical site. The fixation member 56 may be arranged to oppose shear forces experienced by the implant 50 subsequent to implantation. Various fixation members may be utilized, such as posts, pegs, keels, etc. One or more guide elements may be utilized to guide the implant 50 or one or more surgical instruments for preparing a bone to position the fixation member(s) 56 in the bone. In the implementation of FIGS. 3A and 3C-3E, the fixation member 56 may be an elongated post. The fixation member 56 may extend along a fixation (e.g., longitudinal) axis AA. One of the internal walls 55 may establish the fixation member 56 (e.g., FIGS. 3D-3E). The fixation member 56 may be dimensioned to extend from the rear face 51B of the implant 50. An aperture 54 may be dimensioned to extend through the fixation member 56, such as the intermediate aperture 541. An implant passage 59 may be dimensioned to extend through the fixation member 56 and may extend along the fixation axis AA. In implementations, all implant passages 59 of the implant 50 may have respective minimum cross sectional areas that may be less than a minimum cross sectional area of any of the apertures 54 of the implant 50. The fixation axis AA may be collinear with, or may otherwise be parallel to, the implant axis X. In the implementation of FIG. 4, implant 150 may include a fixation member 156 dimensioned such that the fixation axis AA may be offset from, or may be transverse to, the implant axis X. In the implementation of FIG. 5, implant 250 may include a plurality of fixation members 256. The fixation members 256 may be dimensioned such that each fixation axis AA may be offset from, or may be transverse to, the implant axis X.

Referring to FIG. 3E, with continuing reference to FIGS. 3A-3D, an articulation component 57 may be configured to mate with, or may otherwise be secured to, the implant 50 (shown in dashed lines). The articulation component 57 may be secured to the base plate 52 adjacent to the front face 51A of the implant model 32. Various techniques may be utilized to secure the articulation component 57 to the implant 50, such as a Morse taper connection and/or one or more fasteners. The articulation component 57 may include an articular surface 57A dimensioned to cooperate with an adjacent bone or implant. The articular surface 57A may be arranged to mate with an opposed articular surface SA (shown in dashed lines). The articular surface SA may be established by the adjacent bone or implant. In implementations, the adjacent bone may be a humerus that opposes a glenoid. The articular surface 57A may have various geometries including a substantially convex or concave geometry. The articulation component 57 may be a glenosphere having a substantially convex articular surface 57A. In other implementations, the articulation component 57 may be omitted, and the front face 51A of the implant 50 may establish the articular surface 57A. The articulation component 57 may be associated with a respective virtual implant model 32 in the form of a virtual articulation component.

Figure 6A:
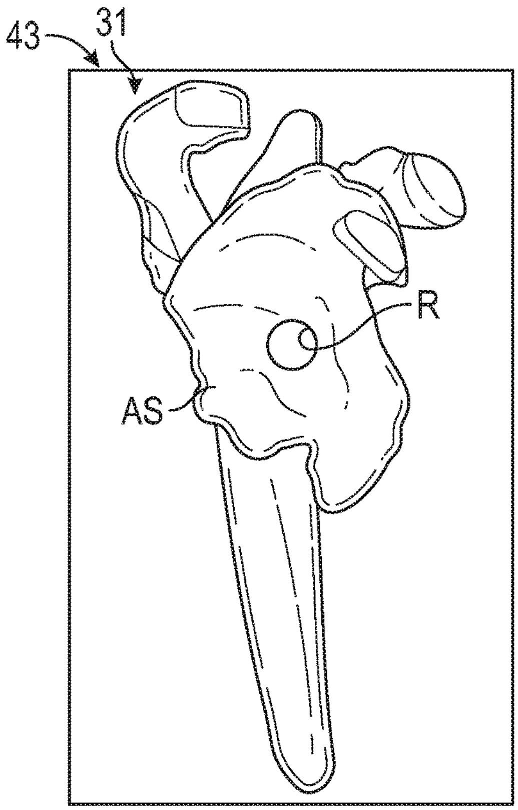
FIGS. 6A-6B disclose a bone model and an implant model positioned relative to the bone model.
Figure 6B:
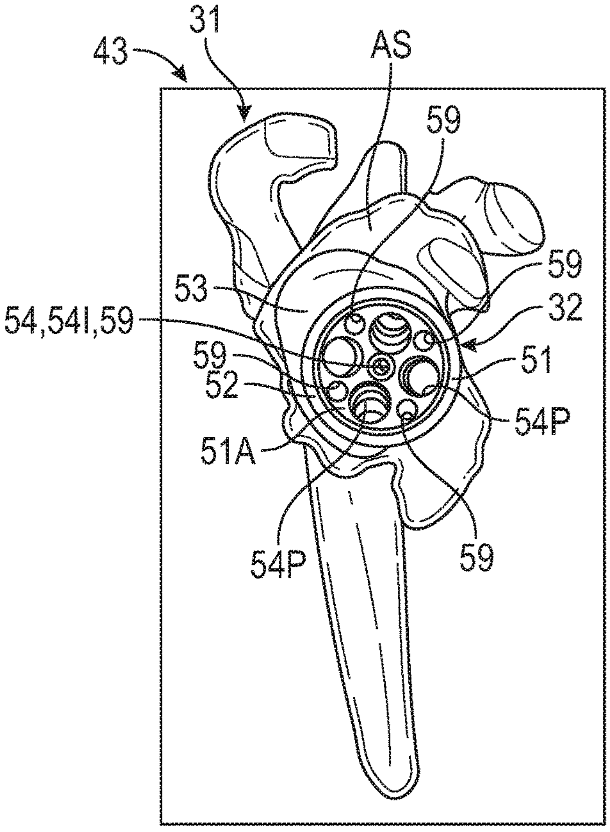

Referring to FIGS. 6A-6B, with continuing reference to FIGS. 2 and 3A-3E, the spatial module 39 may be configured to position the implant model 32 relative to the bone model 31. The bone model 31 may be associated with a scapula of a patient. In the implementation of FIG. 6A, at least one recess R may be established along the articular surface AS and/or another surface of the bone model 31. The articular surface AS may be associated with a glenoid. The recess R may be dimensioned to at least partially receive a respective fixation member 56 for securing the implant to the respective bone (e.g., FIG. 7).

Figure 7:
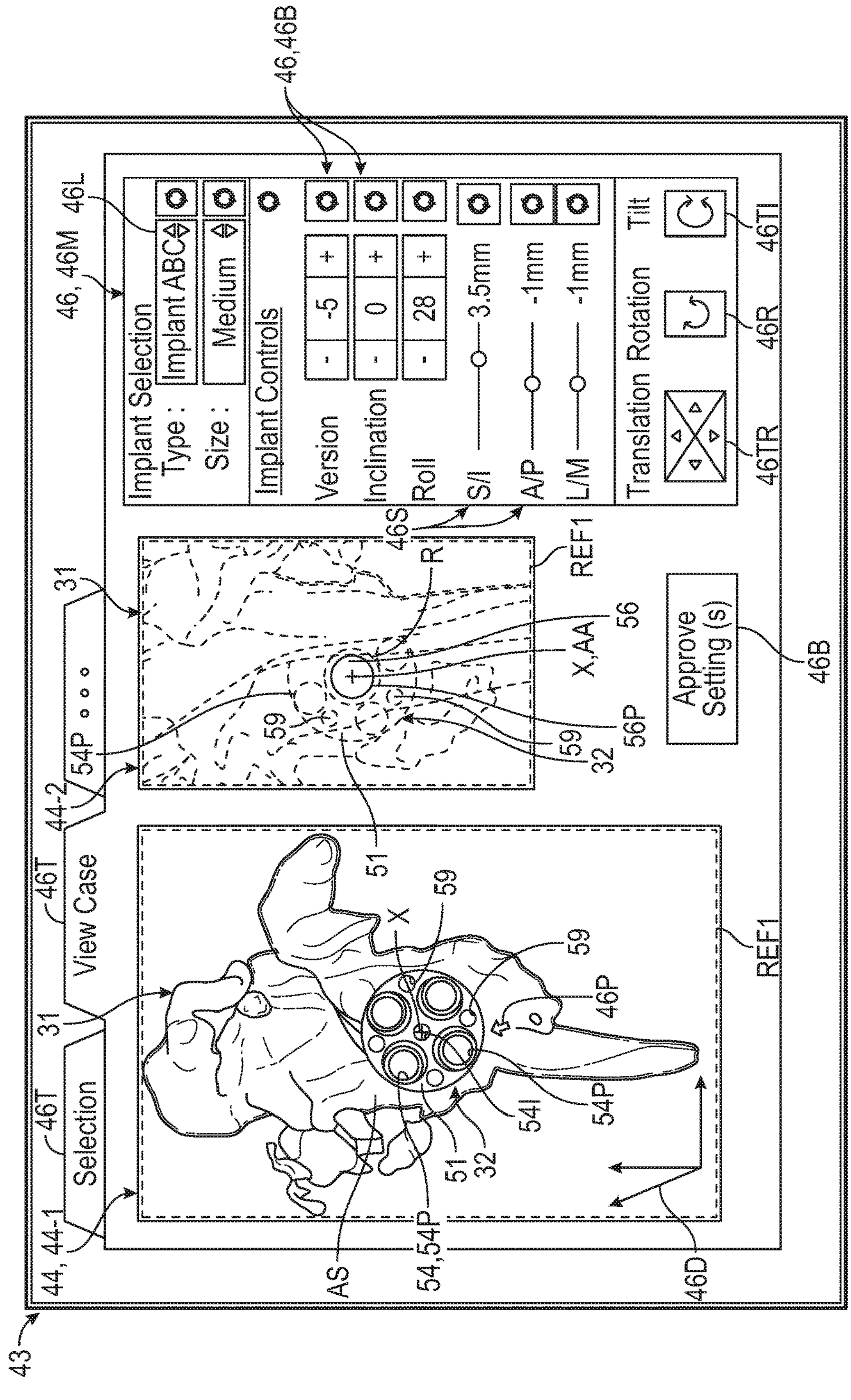
FIGS. 7-9 disclose an implant model at various positions relative to a bone model in display windows of the user interface of FIG. 2.

Referring to FIG. 7, with continuing reference to FIGS. 2 and 3A-3E, the user interface 43 may include a first display window 44-1 and/or a second display window 44-2. Fewer or more than two display windows 44 may be utilized in accordance with the teachings disclosed herein. Geometric objects, including selected virtual bone model(s) 31, implant model(s) 32, transfer model(s) 48 (e.g., FIG. 10) and/or other information relating to a surgical plan 33 may be displayed in one or more of the display windows 44.

The user interface 43 may include one or more objects 46, which may be linked to or otherwise associated with the display window(s) 44. The objects 46 may include graphics such as menus, tabs, lists, entry fields and buttons accessible by user interaction, such as tabs 46T, buttons 46B, drop-down lists 46L, menus 46M, directional indicators 46D, sliders 46S, translational button 46TR, rotation button 46R and/or tilt button 46TI. The objects 46 may include a pointer 46P associated with a mouse or other input device. In implementations, one or more entries may be specified in respective entry fields, including any parameters associated with the lists 46L.

A surgeon or clinical user may interact with the user interface 43 to retrieve, view, edit, store, etc., various aspects of a surgical plan 33, such as the selected bone model(s) 31, implant model(s) 32 and/or transfer model(s) 48. The surgeon or clinical user may interact with the objects 46, display window(s) 44 and/or another portion of the user interface 43 to select one or more implant models 32. Various parameters may be utilized to select the implant model 32, such as surgical procedure, anatomy, type, size, etc. The surgeon or clinical user may interact with the objects 46, directly with the display window(s) 44 (e.g., with the pointer 46P) and/or another portion of the user interface 43 to adjust or otherwise define the position of the implant model 32 relative to the bone model 31.

The planning environment 27 may be configured to define a position of a virtual implant model 32 relative to a virtual bone model 31. The planning environment 27 may be configured to cause the implant model 32 to be displayed in the graphical user interface 43 relative to the bone model 31. The spatial module 39 may be configured to set a position of the main body 51 of the implant model 32 relative to the bone model 31.

The planning environment 27 may be configured to define one or more aspects of the implant model 32, including a geometry and/or position of the implant model 32 relative to the bone model 31. The planning environment 27 may be configured to establish one or more apertures 54, fixation members 56 and/or implant passages 59 in the implant model 32. The planning environment 27 may be configured to define a geometry of each fixation member 56, including defining a size and/or shape of the fixation member 56. The teachings disclosed herein may be utilized to establish fixation members for treating any of the bones and joints disclosed herein, including the glenoid of a shoulder joint. The disclosed techniques may be utilized to establish fixation members for implants associated with other bones and joints, such an implant associated with a tibia plateau or hip, a stem of an implant insertable in a femur or humerus, etc.

The spatial module 39 may be configured to set a position of the main body 51 of the implant model 32 relative to the bone model 31 and/or a first reference plane REF1. The reference plane REF1 may be established relative to one or more directions and/or landmarks of the anatomy. In implementations, the reference plane REF1 may extend in a superior-inferior (S/I) direction and/or anterior-posterior (A/P) direction of the anatomy. The spatial module 39 may be configured to adjust the position and/or orientation of the implant axis X and/or fixation axis AA in response to translating, rotating and/or tilting the implant model 32. The surgeon or clinical user may interact with the user interface 43 to adjust or otherwise define the roll, inclination and/or version of the implant model 32.

The spatial module 39 may be configured to adjust the position of the implant model 32 in one or more directions associated with the anatomy. The directions may include the S/I direction, A/P direction and/or lateral-medial (L/M) direction of the anatomy. The spatial module 39 may be configured to adjust a position of each aperture 54 and/or implant passage 59 in response to translating and/or rotating the implant model 32 relative to the respective implant axis X. The surgeon or clinical user may interact with the objects 46, directly with the display window(s) 44-1, 44-2 and/or another portion of the user interface 43 to adjust or otherwise define the position and/or orientation of the implant model 32 relative to the bone model 31 and/or reference plane REF1. The surgeon or clinical user may interact with the user interface 43 to position the fixation member(s) 56 and/or apertures 54 for receiving respective fasteners to improve fixation based on a geometry and/or quality of the respective bone.

The surgeon or clinical user may interact with a button 46B and/or another portion of the user interface 43 to approve the setting(s) associated with the implant model 32, including the implant selection, position and/or orientation relative to the bone model 31.

Figure 8:
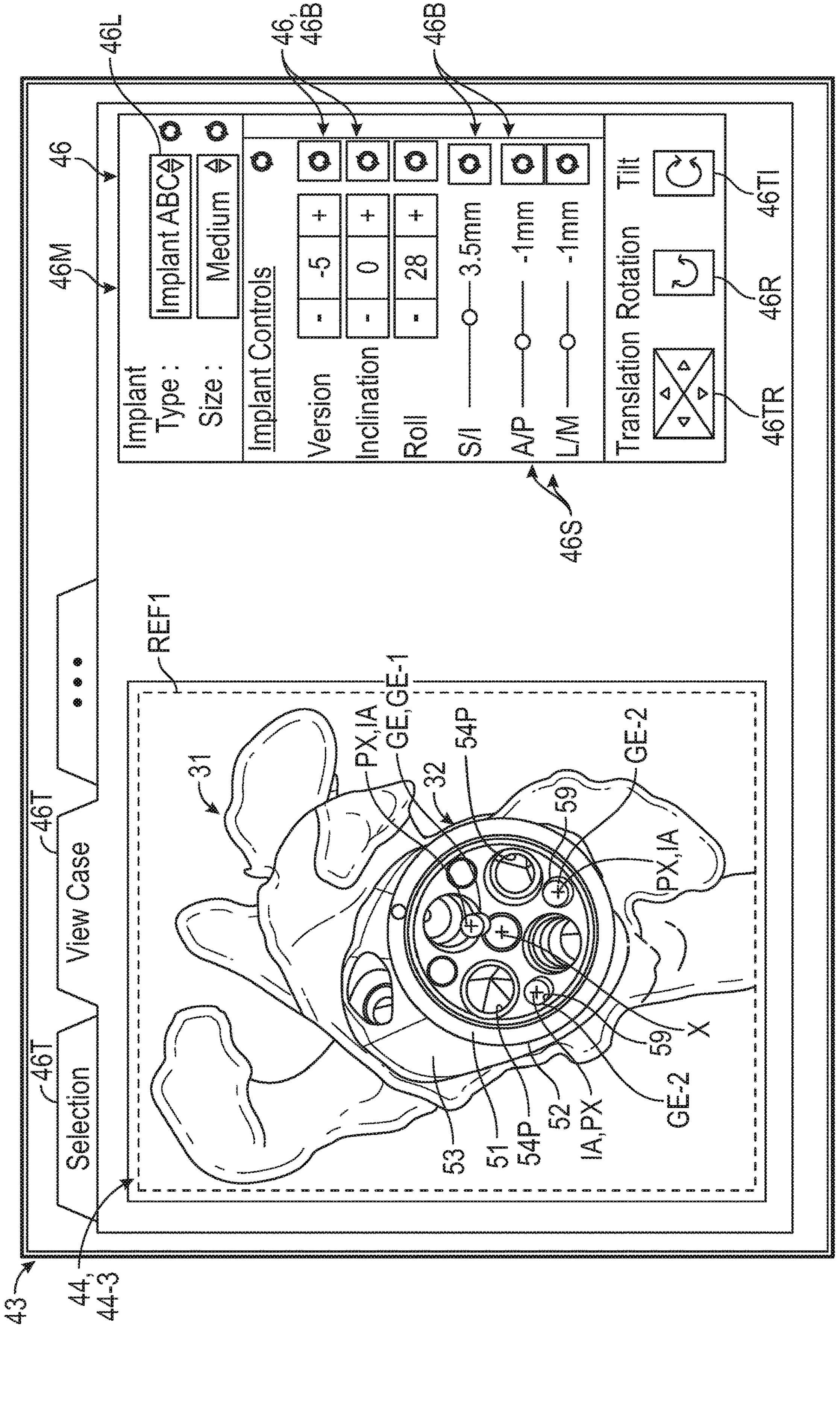
Figure 9:
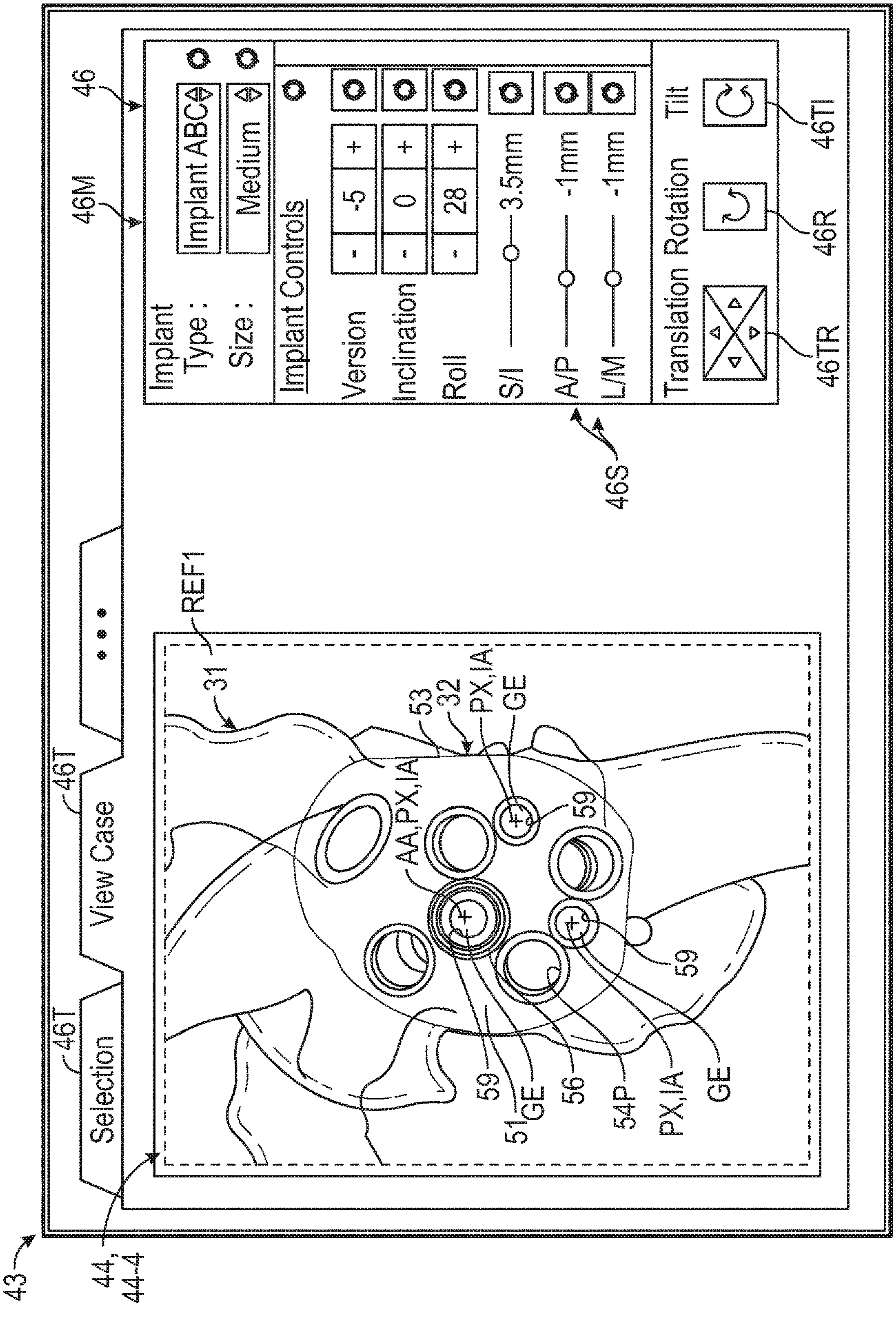

Referring to FIGS. 8-9, with continuing reference to FIGS. 2 and 7, the user interface 43 may include a third display window 44-3 (FIG. 8) and a fourth display window 44-4 (FIG. 9). In implementations, the planning environment 27 may be configured to define a geometry of the augment 53 (e.g., FIGS. 3A-3E and 8-9). The geometry of the augment 53 may be established in response to setting a position of the implant model 32 relative to the bone model 31. The spatial module 39 may be configured to generate a volume of the augment 53 and/or a position and/or trajectory of one or more guide elements GE and/or associated (e.g., insertion) axes IA. In implementations, the spatial module 39 may be configured to generate the volume of the augment 53 and/or the position and/or trajectory of the guide element(s) GE and/or associated insertion axes IA automatically and/or in response to approval of the implant setting(s). The spatial module 39 may be configured to generate one or more implant passages 59 in the volume of the augment 53 based on the position and/or trajectory of the guide element(s) GE, or vice versa. The implant passages 59 may be dimensioned to extend along respective passage axes PX (see also FIGS. 3E and 31-35). The spatial model 39 may be operable to establish the insertion axes IA of the respective guide elements GE based on the arrangement of the implant passages 59 relative to the bone model 31. The spatial model 39 may be operable to establish the insertion axes IA of the respective guide elements GE relative to the bone model 31 such that the insertion axes IA may be substantially aligned with, or may be otherwise parallel to, the respective passage axes PX, or vice versa.

Referring to FIG. 10, with continuing reference to FIGS. 2 and 7-9, the user interface 43 may include a fifth display window 44-5. The spatial module 39 may be operable to position the transfer model 48 relative to the bone model 31 and/or implant model 32. The surgeon or clinical user may interact with the menu 46M, directly with the display window 44-5 using the pointer 46P and/or with another portion of the user interface 43 to select various settings associated with the transfer model 48. In implementations, the user may select a total number of locating arms 72 associated with the transfer model 48. The user may interact with the user interface 43 to specify one or more points (e.g., landmarks) P associated with each of the respective locating arms 72 (e.g., points P-1 to P-6) along or otherwise relative to the bone model 31. The spatial module 39 may be operable to extrude the locating arm 72 along a reference plane extending between a guide (e.g., main) body 70 of the transfer model 48 and the respective point P (see, e.g., FIG. 11). The main body 70 may establish a locating passageway 70P for receiving a bushing 66 to set a trajectory of one or more guide elements GE. The bushing 66 may be associated with the transfer model 48 and/or surgical plan 33. The user may interact with the user interface 33 to specify one or more contact points (e.g., landmarks) CP associated with each of the respective locating arms 72 (e.g., points CP-1 to CP-6) along or otherwise relative to the bone model 31. The spatial module 39 may be operable to extrude a contact surface of the locating arm 72 along the reference plane to the respective contact point CP (e.g., contact surface 172C of FIG. 20). The surgeon or clinical user may interact with a button 46B and/or another portion of the user interface 43 to approve the setting(s) associated with the transfer model 48. The contact surfaces of the locating arms 72 may be patient-specific and may be dimensioned to follow a bone contour of a bone associated with the bone model 31, such as an articular surface and/or a non-articular surface of the bone of a patient.

Figure 11:
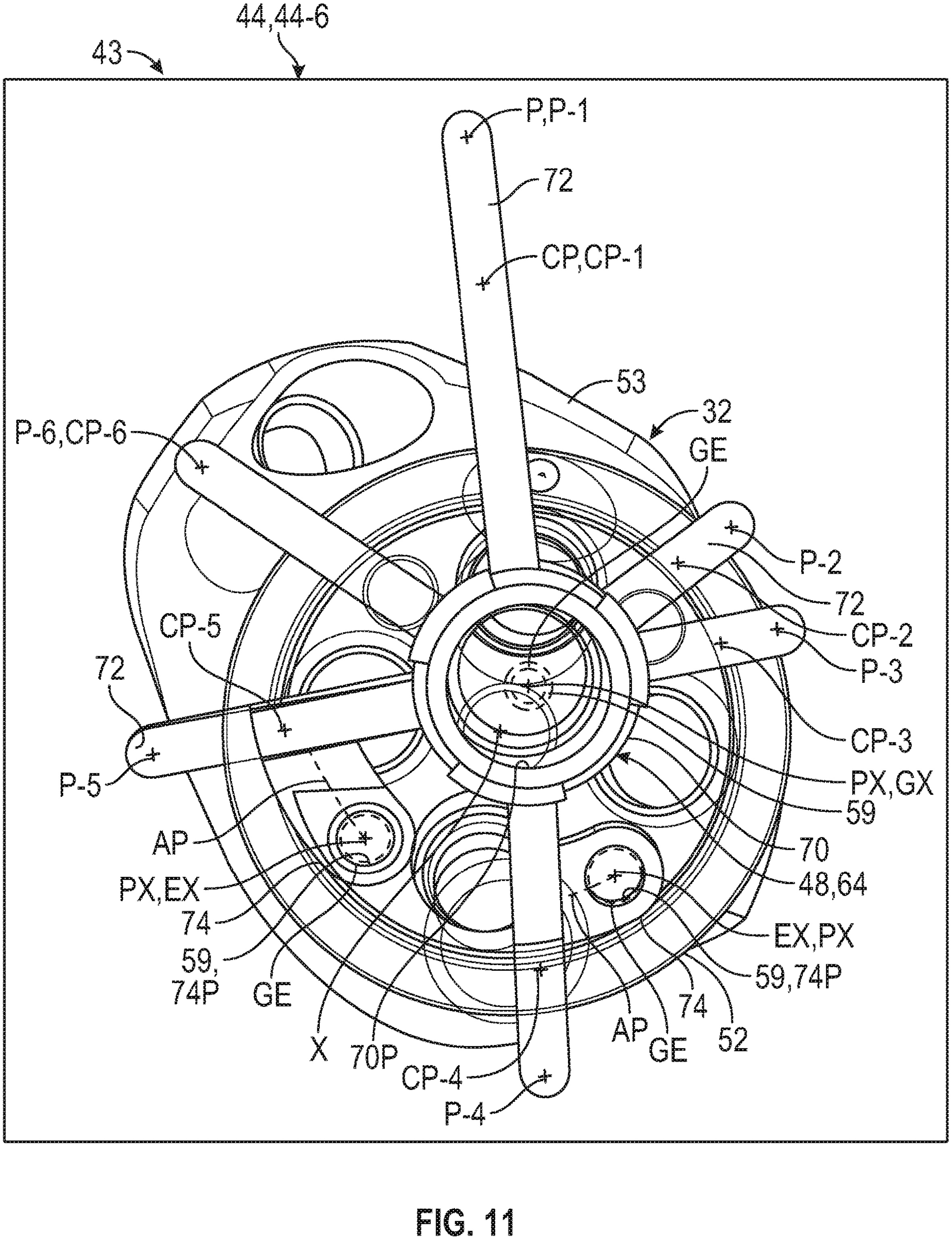
FIG. 11 discloses an isolated view of the transfer model and implant model of FIG. 10.

Referring to FIG. 11, with continuing reference to FIGS. 2 and 7-10, the user interface 43 may include a sixth display window 44-6. The transfer model 48 may include one or more extensions 74. The spatial module 39 may be operable to establish one or more extensions 74 and associated guide passage(s) 74P in the transfer model 48, which may be associated with respective implant passages 59 of the implant model 32. The extensions 74 may extend from a respective locating arm 72. The extensions 74 may extend circumferentially from one or more of the locating arms 72 relative to the guide axis GX of the locating component 64. Each extension 74 may include at least one guide passage 74P. The spatial module 39 may be operable to establish the extensions 74 and associated guide passages 74P utilizing any of the techniques disclosed herein.

The extension 74 may have a substantially arcuate geometry. The extension 74 may be dimensioned to follow an arc (e.g., circumferential) path AP. The arc path AP may be dimensioned to extend about the guide axis GX of the locating component 64. The spatial module 39 may be operable to establish the extension 74 by extruding (e.g., sweeping) a volume of the extension 74 along the arc path AP from a respective one of the locating arms 72. The spatial module 39 may be operable to set a position of one or more guide passages 74P along the arc path AP of the extension 74. The spatial module 39 may be operable to establish at least one guide passage 74P of the extension 74 along the arc path AP. The position of the guide passage 74P may be established along the arc path AP such that the guide passage 74P may be substantially aligned with a position of a passage axis PX of an associated implant passage 59 of the implant model 32. The spatial module 39 may be operable to overlay a volume of the transfer model 48 and a volume of the implant model 32 in the user interface 43 for establishing a geometry and features of the transfer model 48. In implementations, positions of the respective locating arms 72 relative to the main body 70 of the locating component 64 may be set or otherwise defined prior to the positions of the guide passages 74P in the extensions 74. The transfer model 48 may be dimensioned by setting the position of the guide passage 74P along the arc path AP subsequent to setting a circumferential position of the respective locating arm(s) 72 relative to the guide axis GX.

Neighboring locating arms 72 may establish respective circumferential offsets relative to the guide axis GX. Neighboring implant passages 59 may establish respective circumferential offsets relative to the implant axis X of the implant 50. The circumferential offsets may be the same or may differ from each other. In the implementation of FIG. 11, the circumferential offset(s) between the neighboring locating arms 72 associated with the guide passage(s) 74P may differ from the circumferential offset(s) between the respective neighboring implant passages 59.

Figure 12:
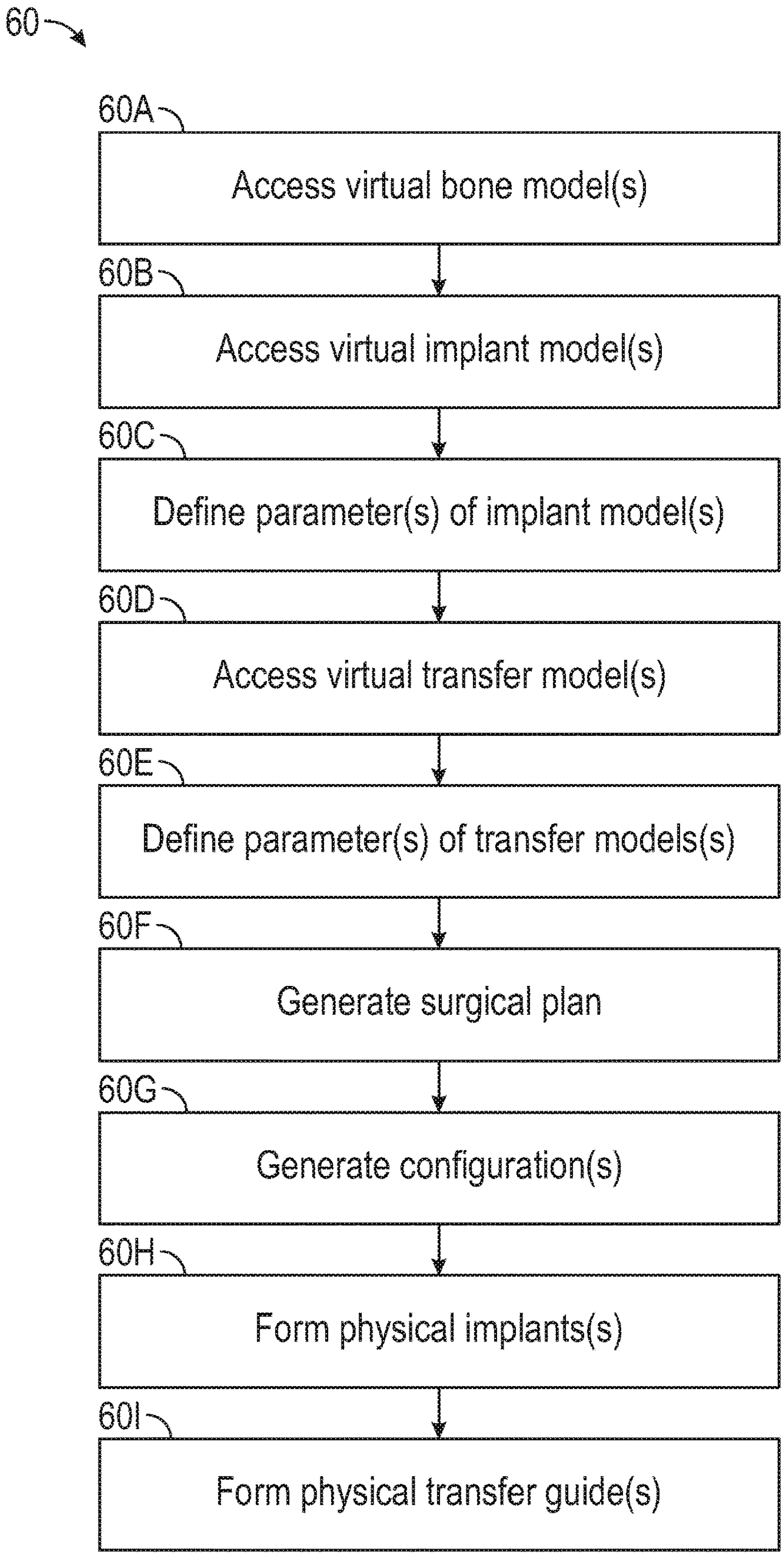
FIG. 12 discloses a method of establishing an implant according to an implementation.

FIG. 12 discloses a method of establishing (e.g., forming) an implant and/or orthopaedic (e.g., transfer) guide for a surgical procedure in a flowchart 60. The implant(s) and/or guide(s) may be utilized to perform an arthroplasty for restoring functionality to various bones and joints, including any of the bones and associated joints disclosed herein such as shoulder, ankle, hip, knee and elbow joints. In implementations, the implant(s) and/or guide(s) may be utilized to perform an arthroplasty for restoring functionality to shoulders having advanced cartilage disease, such as repairing bone defects along a glenoid. The method may be utilized to establish any of the implants and transfer guides disclosed herein. Fewer or additional steps than are recited below could be performed within the scope of this disclosure, and the recited order of steps is not intended to limit this disclosure. It should be understood that the planning environment 27 and any of the associated modules may be configured to perform any of the functionality of the method 60.

Referring to FIG. 2, with continuing reference to FIG. 12, one or more virtual anatomical (e.g., bone) models 31 may be selected or otherwise accessed from memory at step 60A. The bone models 31 may include any of the bone models disclosed herein. Each bone model 31 may be associated with a bone of a respective patient or may be a bone model representative of a hypothetical case. The bone model 31 may be associated with soft tissue, including muscle, ligaments, tensions, skin, etc.

At step 60B, one or more virtual implant models 32 may be selected or otherwise accessed from memory. The implant models 32 may include any of the implant models disclosed herein. Each implant model 32 may have a patient-specific geometry associated with a respective patient or may have a non-patient specific geometry for treating different patients. In the implementation of FIGS. 3A-3E, the implant model 32 may be representative of the implant 50. The implant model 32 may include a main (e.g., implant) body 51 extending between a front face 51A and a rear face 51B. The implant model 32 may include one or more apertures 54 and/or implant passages 59 extending through the main body 51. Each of the apertures 54 may be dimensioned to receive a respective fastener F (e.g., FIG. 3E). The implant model 32 may include at least one fixation member 56 extending from the main body 51. Each fixation member 56 may extend from the rear face 51B of the implant body 51. The fixation member 56 may be dimensioned to secure or otherwise position the implant 50 relative to the bone. Each implant passage 59 may be dimensioned to receive a guide element for positioning the physical implant on the anatomy.

Referring to FIG. 7, with continuing reference to FIGS. 2 and 12, one or more parameters associated with the implant model(s) 32 may be specified or otherwise defined at step 60C. Step 60C may include defining a position of the implant model 32 relative to the respective bone model 31 associated with a bone of a patient. Step 60C may include defining, in a surgical plan 33 for a patient, a position of the implant model 32 relative to an articular surface AS of the bone model 31. Various techniques may be utilized to position the implant model 32, including any of the techniques disclosed herein. Step 60C may include translating, rotating and/or tilting the implant model 32 relative to the bone model 31 to establish a defined position and/or orientation of the implant model 32.

Referring to FIGS. 8-9, with continuing reference to FIGS. 2, 7 and 12, step 60C may include defining a geometry of the implant model 32, which may include any of the features disclosed herein. The geometry of the implant model 32 may be defined utilizing any of the techniques disclosed herein. Defining the geometry may occur prior to, concurrently with, and/or subsequent to defining a position and/or orientation of the implant model 32. Method 60 may include repeating one or more iterations of step 60C prior to approval of a surgical plan 33 associated with the respective bone model(s) 31 and/or implant model(s) 32. Step 60C may include defining a quantity, position and/or orientation of aperture(s) 54 and/or implant passages 59 that may be dimensioned to extend at least partially or completely through the main body 51 of the implant model 32. Step 60C may include defining the geometry of the virtual implant model 32, including the augment 53, such that the rear face 51B may be dimensioned to substantially follow a contour of an articular surface AS associated with the virtual bone model 31 (e.g., FIG. 3E).

Step 60C may include defining a position and/or trajectory of one or more guide elements GE and/or associated insertion axes IA relative to the bone model 31. Step 60C may include substantially aligning the passage axes PX of the implant passages 59 with the insertion axes IA of the respective guide elements GE. The position and/or trajectory of the guide element(s) GE, respective insertion axes IA, and/or associated passage axes PX may be defined utilizing any of the techniques disclosed herein.

Step 60C may include defining a quantity and/or geometry of fixation member(s) 56 for the implant model 32. The quantity and/or geometry of the fixation member(s) 56 may be defined utilizing any of the techniques disclosed herein. Step 60C may include defining a position and/or orientation of the fixation member(s) 56 relative to the main body 51 of the implant model 32. The position and/or orientation of each fixation member 56 may be defined relative to the main body 51 in response to moving the respective fixation member 56 along the first reference plane REF1. Defining the position of the implant model 32 at step 60C may include defining a position and/or orientation of the fixation member(s) 56 relative to the bone model 31. Defining the geometry of the fixation member(s) 56 may include defining various types, shapes and/or dimensions (e.g., length, width, etc.) of the respective fixation member 56 (see, e.g., FIG. 10).

Step 60C may include defining a position and/or trajectory of one or more guide elements GE and/or associated passage axes PX of the implant passages 59 relative to the bone model 31. The position and/or trajectory of the guide element(s) GE and passage axes PX may be defined utilizing any of the techniques disclosed herein.

Step 60C may include specifying or otherwise defining, in the surgical plan 33, a position of a (e.g., first) guide element GE-1 along the articular surface AS of the bone model 31 associated with the bone based on the defined position of the implant model 32 such that an insertion axis IA of the first guide element GE-1 may be substantially aligned with a position associated with a respective fixation member 56. The insertion axis IA of the first guide element GE-1 may be substantially aligned with a position associated with a respective implant passage 59, which may extend at least partially through the fixation member 56.

Step 60C may include specifying or otherwise defining, in the surgical plan 33, a position of a (e.g., second) guide element GE-2 along the articular surface AS of the bone model 31 based on the defined position of the implant model 32 such that an insertion axis IA of the second guide element GE-2 may be substantially aligned with a position associated with a respective implant passage 59.

In implementations, step 60C may include setting or otherwise defining a position and trajectory of the fixation member(s) 156 and associated insertion axis IA of the respective first guide pin GE-1 prior to the setting or otherwise defining a position and trajectory of the insertion axis IA of the second guide pin(s) GE-2.

Referring to FIGS. 10-11, with continuing reference to FIGS. 2, 7-9 and 12, one or more virtual transfer models 48 may be selected or otherwise accessed from memory at step 60D. The transfer model 48 may have a default geometry (e.g., template) associated with one or more implant models 32 that may be modified to implement a surgical plan 33 for a patient.

At step 60E, one or more parameters associated with the transfer model(s) 48 may be set or otherwise defined. The parameters associated with the transfer model 48 may be defined utilizing any of the techniques disclosed herein. Step 60E may include dimensioning a locating component 64 of the transfer model 48 (e.g., FIG. 11), including any of the locating components disclosed herein. The parameters associated with the transfer model 48 may include any of the parameters disclosed herein, including a total number of locating arms 72 and associated point(s) P, CP relative to the bone model 31 (e.g., FIG. 10).

One or more surgical plans 33 may be generated at step 60F. The surgical plan 33 may incorporate information associated with any of the parameters disclosed herein. The surgical plan 33 may include information specifying the position and/or orientation of the respective implant model(s) 32, guide element(s) GE and associated insertion axes IA, and/or transfer model(s) 48 relative to the bone model(s) 31 of a patient. Step 60F may include defining a trajectory associated with one or more fasteners F and/or respective fastener axes FA (e.g., FIG. 3E). Step 60E may include generating the surgical plan 33 associated with the defined position of the virtual implant model 32 and the defined trajectory of the fastener(s) F. The trajectory of each fastener F may be defined according to the position and/or orientation of the implant model 32 and associated apertures 54 defined at step 60C. Step 60F may include defining a trajectory and/or insertion position of an insertion axis IA associated with one or more guide elements GE relative to the bone model 31 (e.g., FIG. 8).

One or more (e.g., implant and/or transfer guide) configurations 47 may be generated at step 60G. The configuration 47 may be associated with a physical implant representative of the implant model 32, such as the implant 50. The configuration 47 may be generated according to the parameters defined at step 60C. In implementations, step 60G may include generating a configuration 47 for a physical surgical (e.g., transfer) guide representative of a transfer model 48 for positioning the physical implant, including any of the transfer guides disclosed herein. The configuration 47 may be generated according to the parameters defined at step 60E. Step 60G may include generating a configuration 47 associated with a physical instance of the locating component 64. The configuration 47 may specify the dimension(s) of the locating component 64.

The physical implant(s) may be formed at step 60H. Step 60H may include forming the physical implant based on the configuration 47 generated at step 60G. The physical implant may be formed utilizing any of the techniques disclosed herein. FIGS. 3A-3E disclose an implementation of a physical implant 50 that may be established based on a respective configuration 47.

The physical transfer guide(s) may be formed at step 60I. Step 60I may include forming the physical transfer guide based on the configuration 47 generated at step 60G. The physical transfer guide may be formed utilizing any of the techniques disclosed herein.

Figure 13:
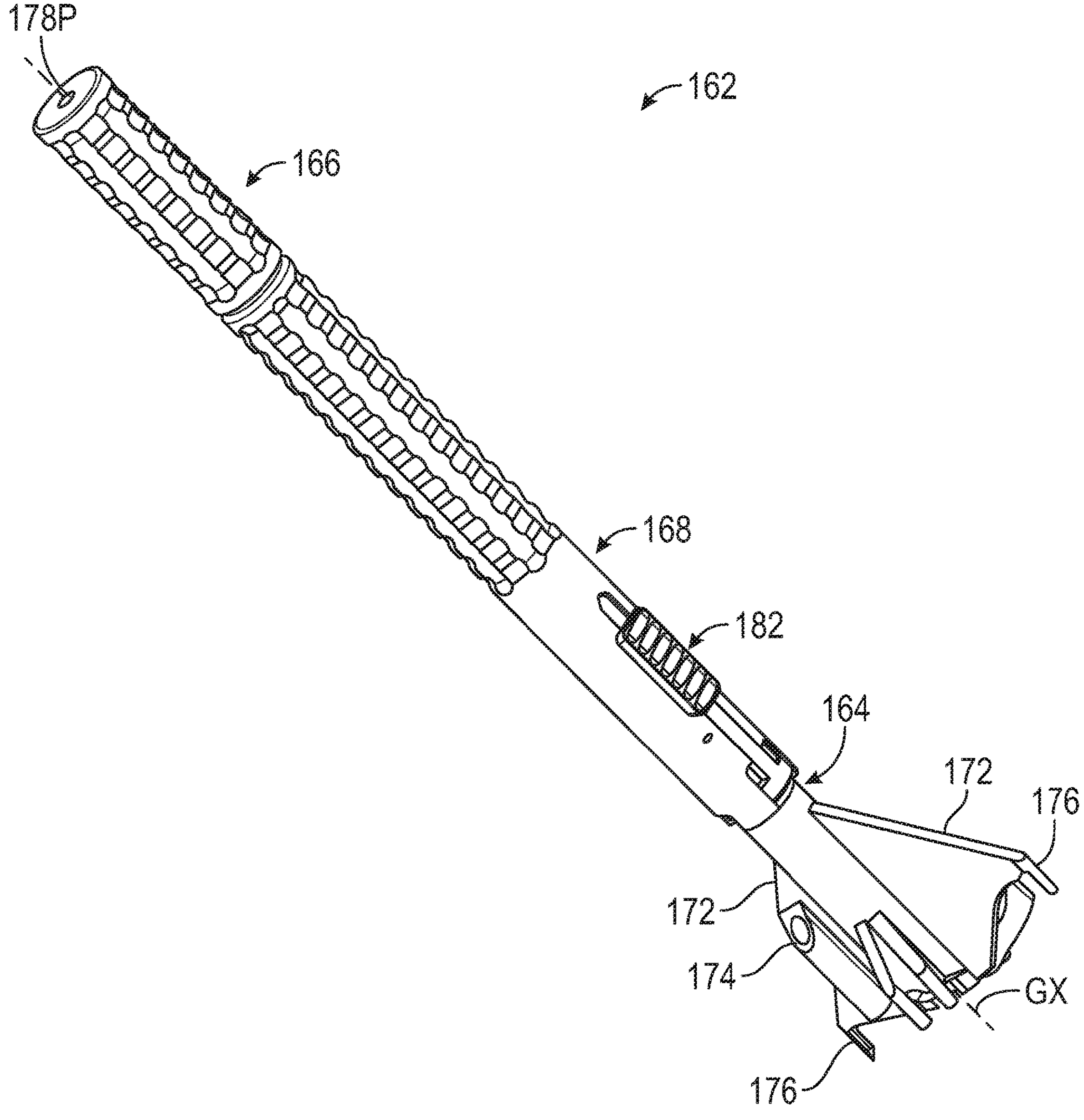
FIG. 13 discloses a surgical guide according to an implementation.

FIGS. 13-19 disclose an implementation of a surgical system including a surgical (e.g., transfer) guide 162. Referring to FIG. 13, with continuing reference to FIG. 2, the transfer guide 162 may be utilized in performing an orthopaedic procedure. The transfer guide 162 may be configured to position one or more implants and/or surgical instruments relative to bone(s) of a patient, including any of the implants and surgical instruments disclosed herein. The implant may be patient-specific. The transfer guide 162 may configured to position one or more guide elements and/or other surgical instruments relative to bone according to a surgical plan 33. The guide element(s) may be utilized to position an implant and/or surgical instrument relative to the bone. The transfer guide 162 may include one or more patient-specific components, which may be associated with the surgical plan 33 of a respective patient. The transfer guide 162 may be associated with a virtual transfer model 48 (e.g., FIGS. 2 and 10). The transfer guide 162 may incorporate any of the features of the transfer models 48 disclosed herein.

The transfer guide 162 may include a locating component 164, bushing 166 and/or sleeve 168. The locating component 164 may be patient-specific. The bushing 166 and/or sleeve 168 may be reusable to treat different patients. The locating component 164, bushing 166 and/or sleeve 168 may be separate components or may be integrally formed. The sleeve 168 may be releasably securable to the locating component 164. The surgeon may be provided with bushings 166 of various shaped and sizes.

The locating component 164, bushing 166 and sleeve 168 may incorporate various metallic and/or non-metallic materials. In implementations, the bushing 166 and/or sleeve 168 may include a first type of material. The locating component 164 may include a second type of material, which may be same or may differ from the first type of material. The first and second types of materials may be metallic or non-metallic. Metallic materials may include a surgical grade steel or alloy. Non-metallic materials may include a biocompatible polymer.

Figure 14:
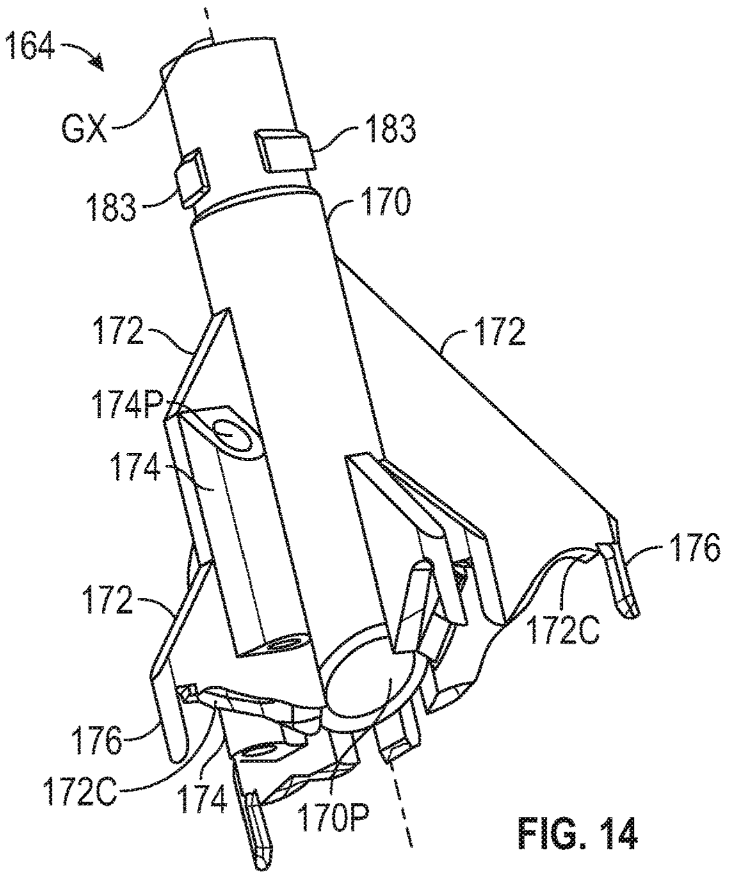
FIGS. 14-16 disclose a locating component of the surgical guide of FIG. 13.
Figure 15:
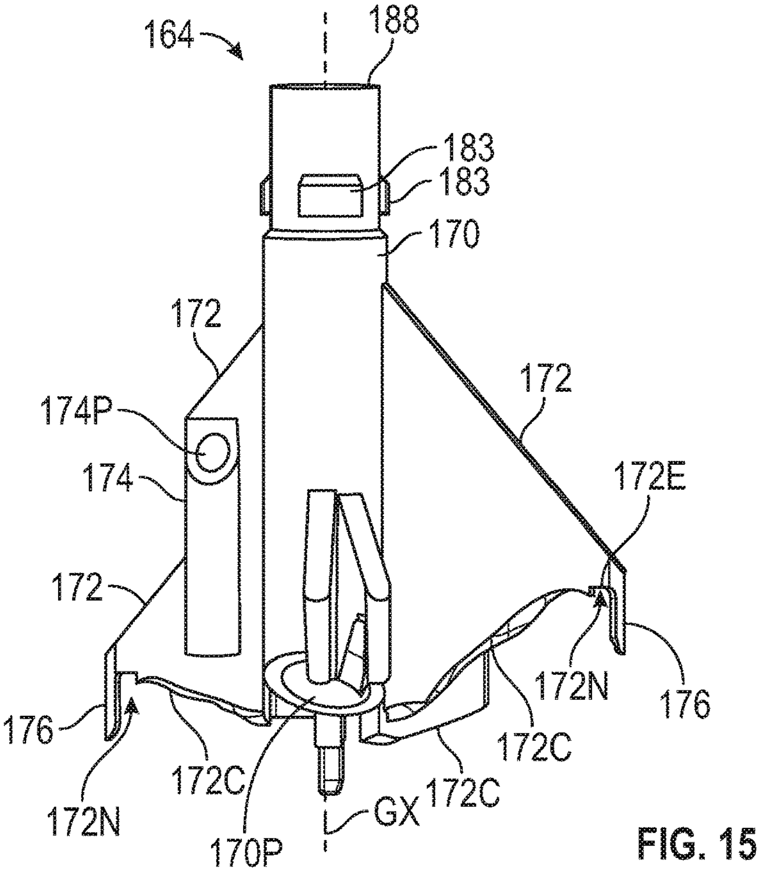
Figure 16:
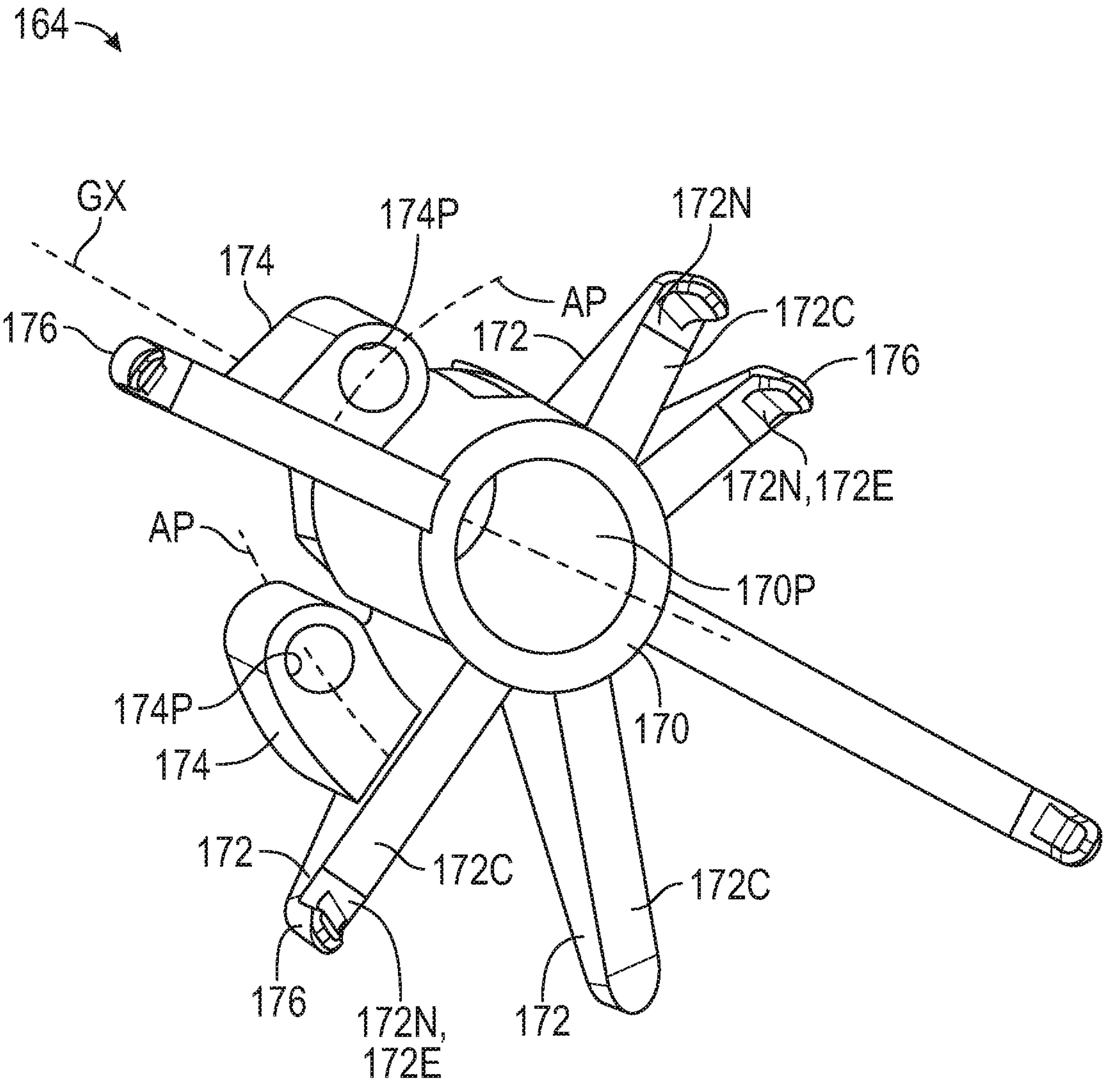

Referring to FIGS. 14-16, with continuing reference to FIGS. 2 and 13, an implementation of the locating component 164 is disclosed. The locating component 164 may be monolithic or may include two or more components attached or otherwise secured to each other. The locating component 164 may include a guide (e.g., main) body 170 and one or more locating members (e.g., arms) 172. The main body 170 may have a tubular geometry. The locating component 164 may include a locating passageway 170P in the main body 170 and/or another portion of the locating component 164. The locating passageway 170P may extend through the main body 170. The locating passageway 170P may be dimensioned to extend along a guide axis GX of the locating component 164.

The locating component 164 may include a plurality of locating arms 172 for positioning the locating component 164 on the anatomy. The locating component 164 may have a total of six locating arms 172. In other implementations, the locating component 164 may include fewer or more than six locating arms 172. The locating arms 172 may be dimensioned to extend outwardly from the main body 170. The locating arms 172 may be distributed about, and may be dimensioned to extend from, a periphery of the main body 170. In implementations, the locating arms 172 may be uniformly distributed about the periphery of the main body 170. In other implementations, the locating arms 172 may be non-uniformly distributed about the periphery of the main body 170. In implementations, the locating arms 172 may be dimensioned to extend in a radial direction from the periphery of the main body 170 relative to the guide axis GX.

The locating arms 172 may include respective contact surfaces 172C. The contact surfaces 172C may be patient-specific and may be dimensioned to follow a surface (e.g., bone) contour SC, such as an articular surface AS and/or non-articular surface of the respective bone B of a patient (e.g., FIGS. 20 and 22). The contact surfaces 172C may be discrete. The spaced apart locating arms 172 and discrete contact surfaces 172C may improve positioning of the locating component 164 on the bone B by allowing spaces between the neighboring locating arms 172 to accommodate any soft tissue that may be disposed on the bone B. In other implementations, at least some, or all, of the contact surfaces 172C may be contiguous.

The locating passageway 170P may be dimensioned to receive the bushing 166, which may be dimensioned to receive a (e.g., first) guide element. The locating passageway 170P may be dimensioned to establish a position of the guide element when the contact surfaces 172C may be seated on an (e.g., articular) surface of a bone.

The locating component 164 may include at least one or more extensions 174. The locating component 164 may have a total of two extensions 174. In other implementations, the locating component 164 may include fewer or more than two extensions 174. Each extension 174 may be dimensioned to extend circumferentially from a respective one of the locating arms 172 relative to the guide axis GX. In implementations, two or more extensions 174 may be dimensioned to extend from a common locating arm 172. Each extension 174 may be cantilevered from the respective locating arm 172.

Each extension 174 may include at least one guide passage 174P. The guide passage 174P may be dimensioned to receive a (e.g., second) guide element (e.g., guide elements GE of FIGS. 24-25). A position of the guide element, associated insertion axis and/or guide passage 174P may be based on a position of an implant passage of an implant associated with the associated surgical plan 33 (e.g., guide elements GE and insertion axes IA of FIG. 10).

Various techniques may be utilized to dimension the extension(s) 174, including any of the techniques disclosed herein. The extension 174 may have a substantially arcuate geometry. The extension 174 may be dimensioned to follow an arc (e.g., circumferential) path AP about the guide axis GX (e.g., FIG. 16). The extension 174 may be dimensioned by extruding (e.g., sweeping) a volume the extension 174 along the arc path AP from a respective one of the locating arms 172. The extension 174 may include at least one guide passage 174P along the arc path AP. The guide passage 174P may establish the position of a (e.g., second) guide element when the contact surfaces 172C may be seated on the (e.g., articular) surface of the bone. The position of the guide passage 174P may be established along the arc path AP such that the guide passage 174P may be substantially aligned with a position of an associated implant passage 59 relative to a bone when the locating component 164 may be seated on a bone contour of the bone (e.g., FIG. 10).

The arc paths AP of two or more of the respective extensions 174 may have a common radius including an origin associated with an implant axis X of the implant 50. In the implementation of FIGS. 10-11, the common radius may have an origin along the implant axis X.

The locating component 164 may include at least one or more overhangs 176. Each overhang 176 may be dimensioned to extend from an end portion of a respective one of the locating arms 172. Each overhang 176 may be dimensioned to contact a (e.g., non-articular) surface of a bone to limit (e.g., translational and/or rotational) movement of the locating component 164 relative to a bone when the contact surfaces 172C may be seated on an (e.g., articular) surface of the bone having an associated (e.g., patient-specific) bone contour.

In implementations, the patient-specific contact surfaces 172C may be dimensioned to terminate prior to the respective overhangs 176, which may improve seating the locating component 164 on the bone in a patient-specific position. The patient-specific position may be specified in a surgical plan 33. The locating arm 172 may include a notch 172N separating the respective contact surface 172C and overhang 176 (FIGS. 15-16). The notch 172N may include an engagement surface (e.g., face) 172E, which may be dimensioned to contact a surface (e.g., rim) of the bone when the respective contact surface 172C may be seated on the bone.

Figure 17:
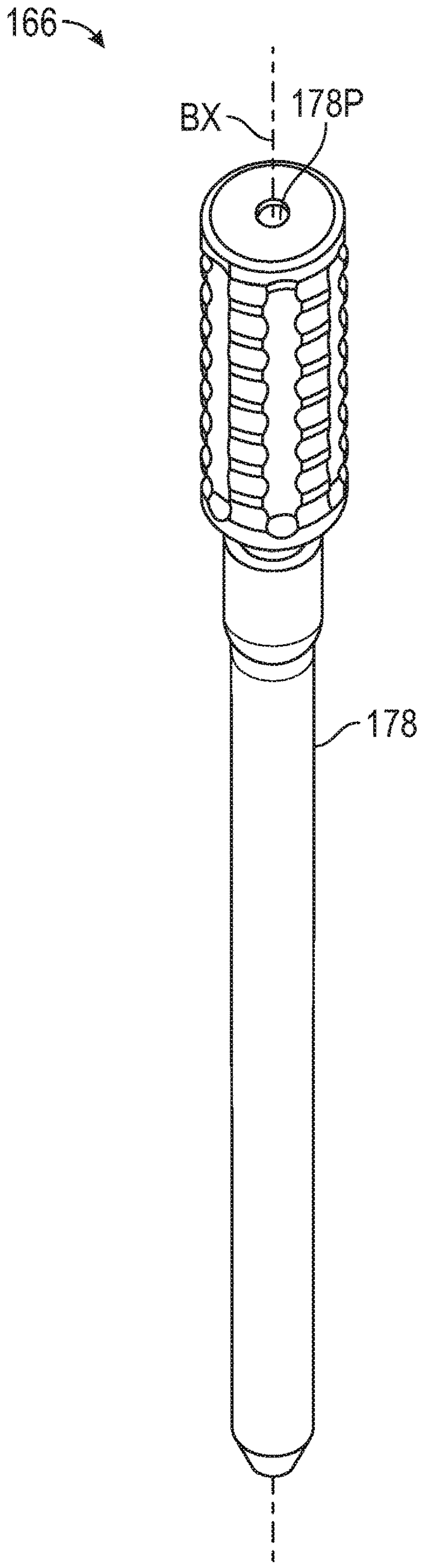
FIG. 17 discloses a bushing of the surgical guide of FIG. 13.

Referring to FIG. 17, with continuing reference to FIGS. 13-16, the bushing 166 may include a bushing body 178. The bushing body 178 may be elongated and may have a tubular geometry. The bushing body 178 may include a bushing passage (e.g., guide bore) 178P. The bushing passage 178P may be dimensioned to receive a (e.g., first) guide element for guiding a surgical instrument, including any of the surgical instruments disclosed herein such as a drill.

Figure 20:
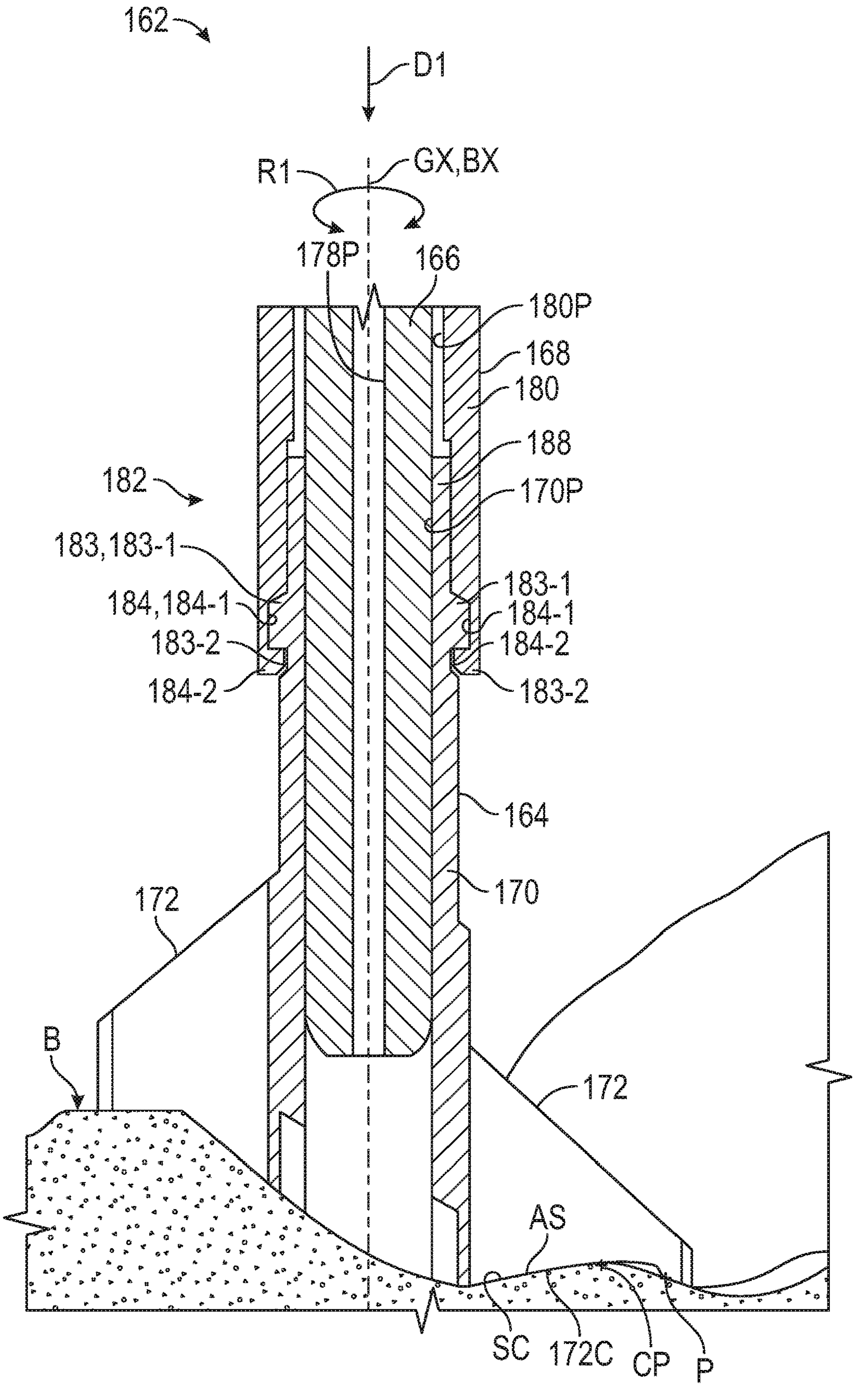
FIGS. 20-21 disclose a locking mechanism of the surgical guide of FIG. 13 according to an implementation.

The locating passageway 170P of the locating component 164 may be dimensioned to at least partially receive the bushing 166 to set a trajectory of the bushing passage 178P (e.g., FIGS. 13 and 20). The bushing passage 178P may extend along a bushing axis BX (see also FIG. 10). In implementations, the locating passageway 170P may be dimensioned to slidably receive the bushing 166 such that the bushing passage 178P may establish a position of a (e.g., first) guide element when the contact surfaces 172C may be seated on an (e.g., articular) surface of the bone.

Figure 18:
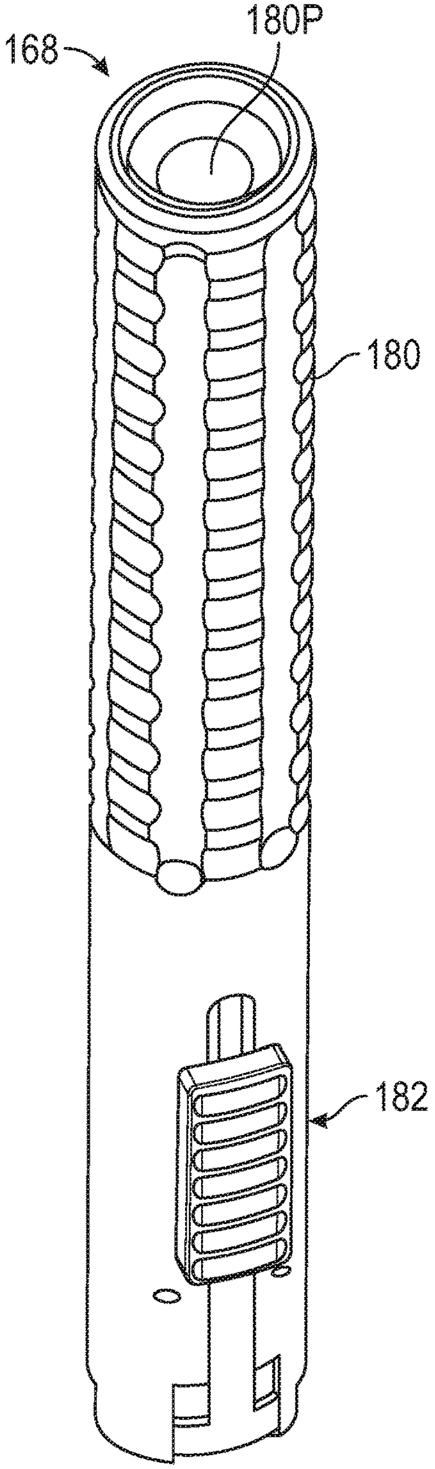
FIG. 18 discloses a sleeve of the surgical guide of FIG. 13.
Figure 19:
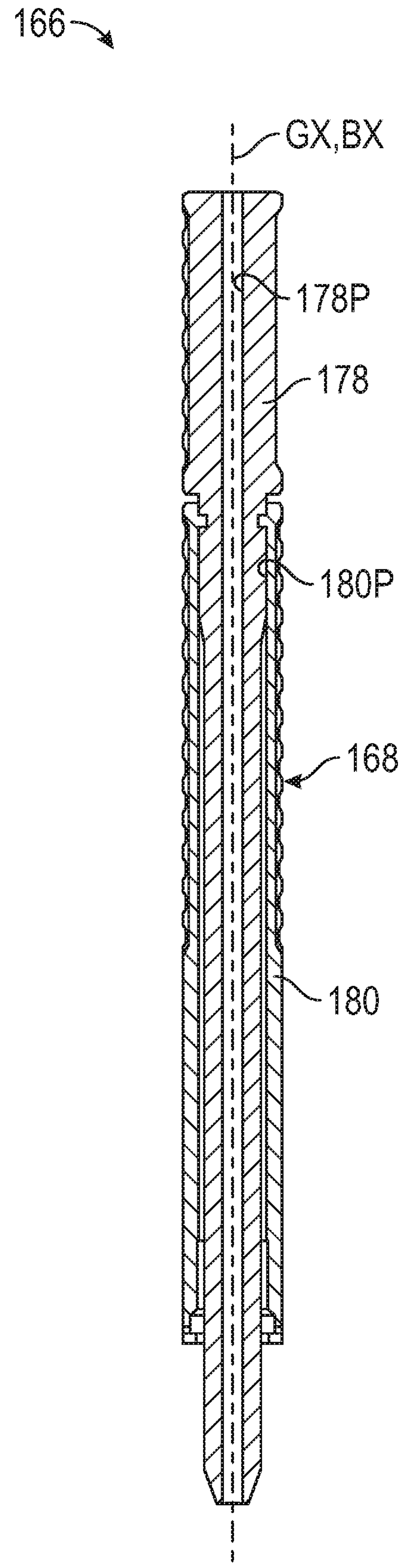
FIG. 19 discloses a sectional view of the bushing and sleeve of the surgical guide of FIG. 13.

Referring to FIGS. 18-19, with continuing reference to FIGS. 13-17, the sleeve 168 may include a sleeve body 180. The sleeve body 180 may be elongated and may have a tubular geometry. The sleeve body 180 may include a sleeve passageway 180P. The sleeve 168 may be releasably securable to a (e.g., proximal) portion of the main body 170 of the locating component 164. In the implementation of FIG. 20, the sleeve passageway 180P and the locating passageway 170P of the bushing 166 may be at least partially aligned with each other and/or with the locating passageway 170P of the locating component 164 in an assembled configuration. The bushing 166 may be at least partially insertable through the sleeve passageway 180P and/or the locating passageway 170P in the assembled configuration to set the trajectory of the bushing passage 178P.

Figure 21:
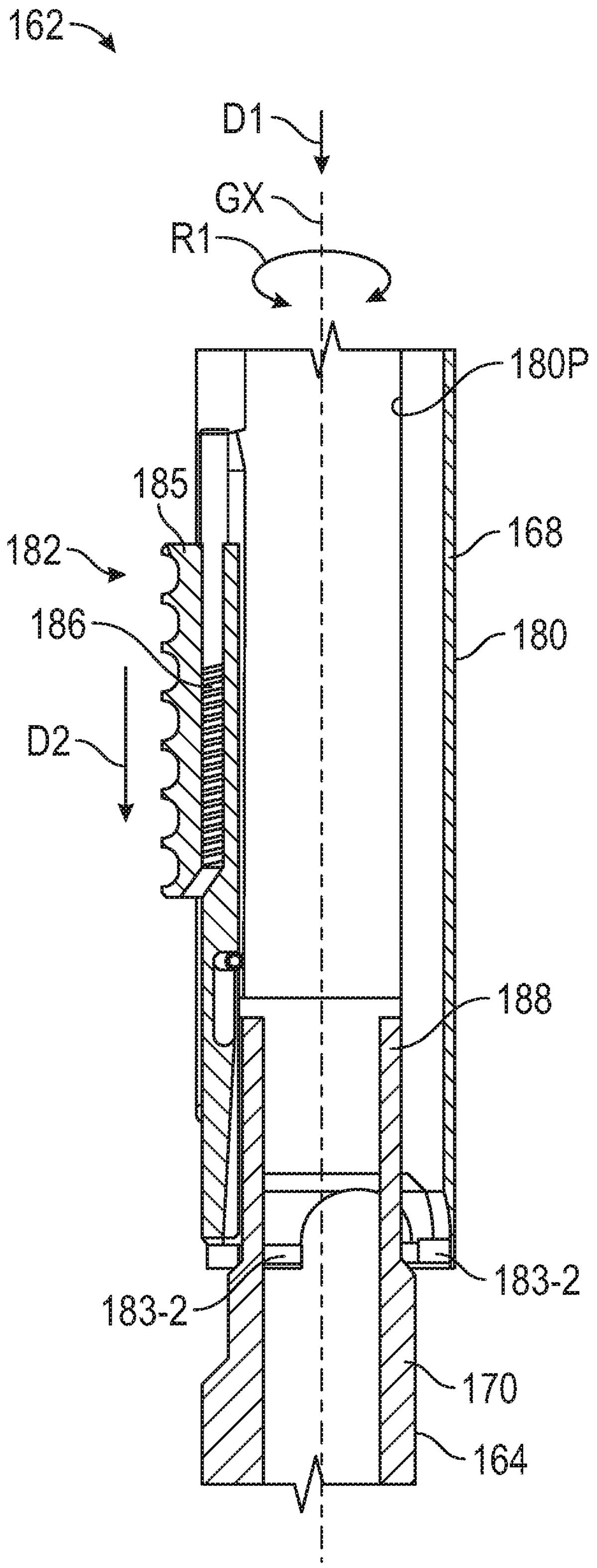

Referring to FIGS. 20-21, with continuing reference to FIGS. 13-19, the transfer guide 162 may include a locking (e.g., twist-lock) mechanism 182 adapted to releasably secure the sleeve 168 and the locating component 164 to each other when in the assembled configuration. Various techniques may be utilized to establish the twist-lock mechanism 182. The twist-lock mechanism 182 may include one or more protrusions (e.g., lugs) 183 dimensioned to engage one or more respective grooves 184. The sleeve 168 may be moveable in a first direction D1 to at least partially receive or otherwise engage a proximal portion of the main body 170 of the locating component 164. The sleeve 168 and locating component 164 may be rotatable in a first rotational direction RI relative to each other such that the protrusions 183 and grooves 184 may engage each other to limit relative (e.g., axial) movement between the locating component 164 and sleeve 168. The first direction D1 may be substantially coaxial or otherwise parallel to the guide axis GX. The first rotational direction RI may be established relative to the guide axis GX.

In implementations, the twist-lock mechanism 182 may include a first set of protrusions 183-1 and/or a second set of protrusions 183-2. The first set of protrusions 183-1 may be dimensioned to engage with a first set of grooves 184-1. The second set of protrusions 183-2 may be dimensioned to engage with a second set of grooves 184-2. The locating component 164 may establish the first set of protrusions 183-1 and/or the second set of grooves 184-2, and the sleeve 168 may establish the second set of protrusions 183-2 and/or the first set of grooves 184-1, or vice versa. Engagement between the protrusions 183 and grooves 184 may limit or otherwise oppose removal of the sleeve 168 from the locating component 164.

In the implementation of FIG. 21, the twist-lock mechanism 182 may include a push-lock 185 adapted to selectively lock the locating component 164 and sleeve 168 together. The push-lock 185 may be moveable between a first (e.g., unlocked) position and a second (e.g., locked) position. A spring member 186 may be arranged to bias the push-lock 185 in a second direction D2 to the locked position.

Figure 22:
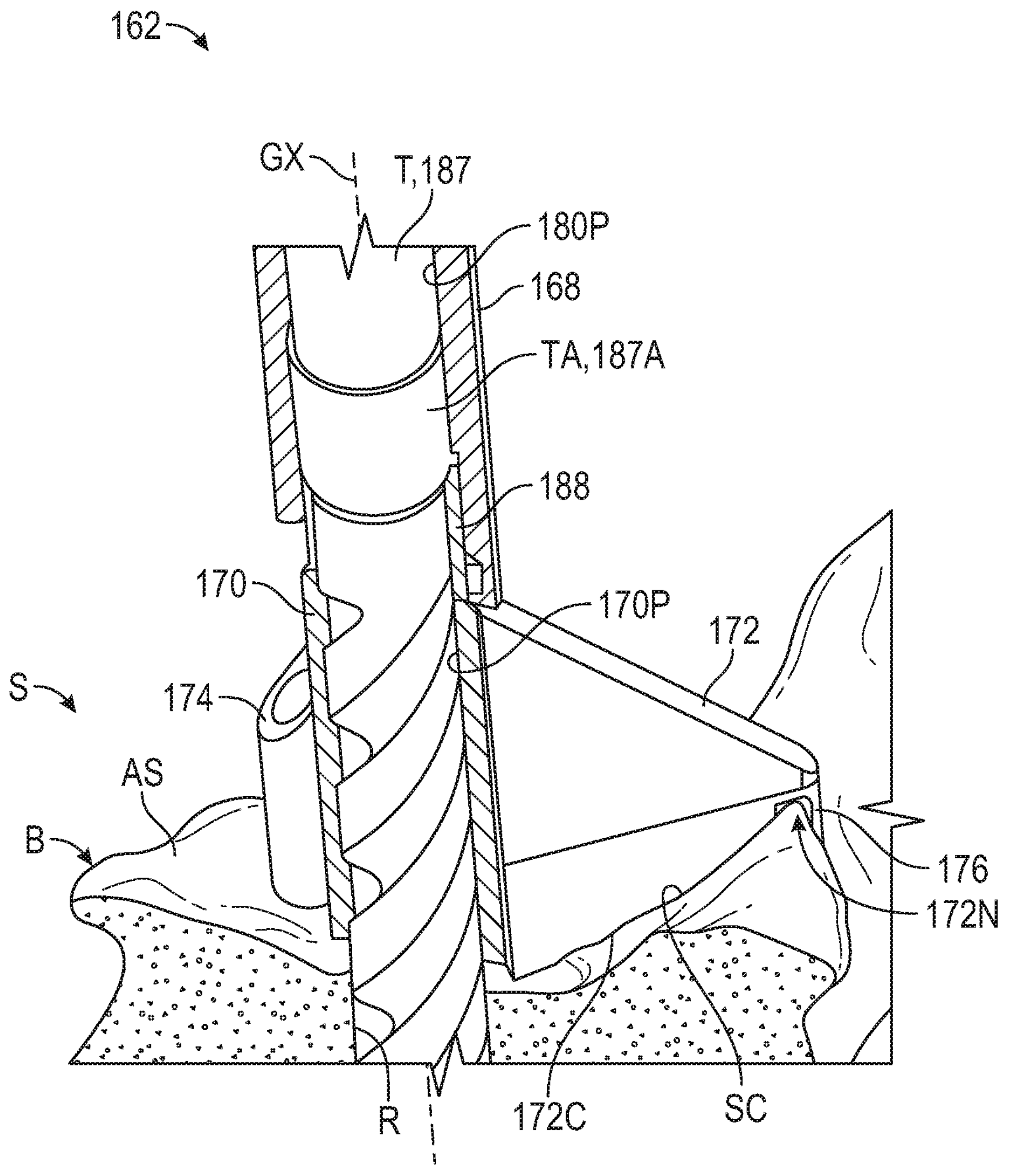
FIG. 22 disclose a surgical tool positioned with the surgical guide of FIG. 13.

Referring to FIG. 22, with continuing reference to FIGS. 13-21, the transfer guide 162 may be adapted to guide or otherwise position various surgical tools (e.g., instruments) relative to the anatomy, including any of the surgical tools disclosed herein. In implementations, the surgical tool may include a punch which may be impacted into the bone to form a recess. The surgical tool may be adapted to remove bone or other tissue from a surgical site S. The surgical tool may be a reamer or burr. The locating passageway 170P may be dimensioned guide the burr along a path including one or more segments to remove tissue at different positions across the bone surface. The surgical tool may be a measurement tool adapted to measure various aspects of the anatomy, including a depth and/or contour of the anatomy and/or a feature formed in the anatomy such as a recess or altered contour (e.g., resected or reamed surface). In implementations, the measurement tool may be adapted to measure a depth of a recess formed in the bone. The transfer guide 162 may include a depth stop 188 dimensioned to limit insertion of a surgical tool (e.g., instrument) T through the locating passageway 170P. The depth stop 188 may be established by the locating component 164. In implementations, the main body 170 of the locating component 164 may be dimensioned to establish the depth stop 188. The depth stop 188 may be established by the main body 170 within the sleeve passageway 180P in an assembled configuration. The depth stop 188 may be established by the locating component 164 adjacent to the twist-lock mechanism 182.

The surgical tool T may be slidably receivable through the sleeve passageway 180P such that an abutment (e.g., shoulder or collar) TA of the surgical tool T may engage the depth stop 188 to limit insertion of the surgical tool T through the locating passageway 170P. An insertion depth of the surgical tool T established by the depth stop 188 may be specified in a surgical plan 33.

In implementations, the surgical tool T may be a drill 187 adapted to remove bone or other tissue from a surgical site S. The locating passageway 170P may be dimensioned to at least partially receive the drill 187. The drill 187 may include an abutment 187A, such as a shoulder or collar, which may be established proximal to a distal tip of the drill. A distance between the abutment 187A and distal tip of the drill 187 may be specified in the surgical plan 33. The depth stop 188 may be dimensioned to limit translation of the drill 187 along an axis of a (e.g., first) guide element for forming a recess R in an (e.g., articular) surface AS of the bone B, which may at least partially receive a fixation member (e.g., fixation member 156 of FIG. 34). The drill 187 may be cannulated for guiding the drill 187 along a guide element (e.g., guide element GE of FIG. 29). The guide element may establish a pilot hole in the bone B prior to forming the recess R for improving positioning of a tip of the drill 187 relative to a surface of the bone B according to a specified position of the fixation member in the surgical plan 33.

Figure 23:
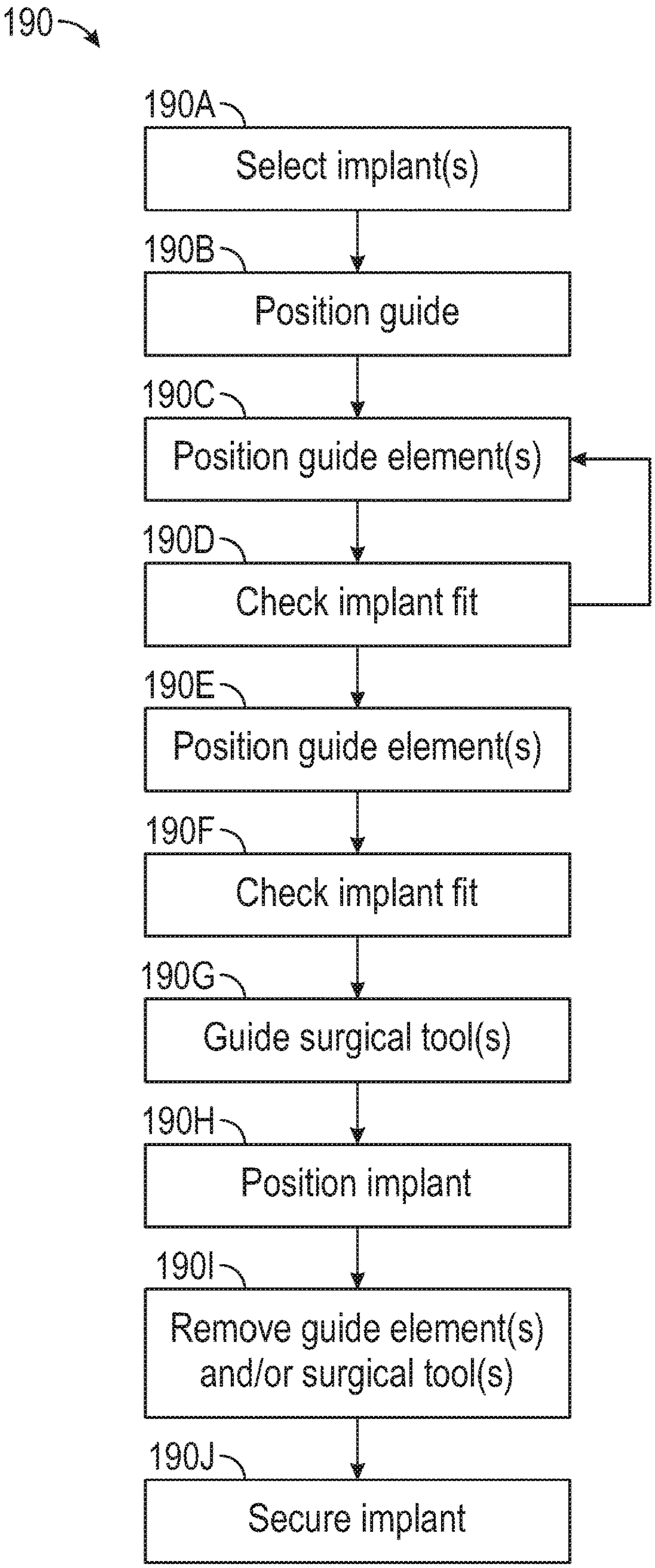
FIG. 23 discloses a method of performing an orthopaedic procedure according to an implementation.

FIG. 23 discloses a method of performing an orthopaedic procedure in a flowchart 190. The method may be utilized to perform an arthroplasty for restoring functionality to various bones and joints, including any of the bones and associated joints disclosed herein such as shoulder, ankle, hip, knee and elbow joints. In implementations, the method may be utilized to perform an arthroplasty for restoring functionality to shoulders having advanced cartilage disease, such as repairing bone defects along a glenoid. The method may be utilized with any of the implants and/or transfer guides disclosed herein. Fewer or additional steps than are recited below could be performed within the scope of this disclosure, and the recited order of steps is not intended to limit this disclosure. It should be understood that the planning environment 27 and any of the associated modules may be configured to perform any of the functionality of the method 190. Reference is made to the transfer guide 162.

Referring to FIG. 2, with continuing reference to FIG. 23, at step 190A a surgeon or other clinical user may select an implant 150 for positioning on a bone of a patient (e.g., FIGS. 31-35). The surgeon may select the implant 150 and/or an associated implant type, size, etc., preoperatively. The implant 150 may be specified in a surgical plan 33.

Figure 24:
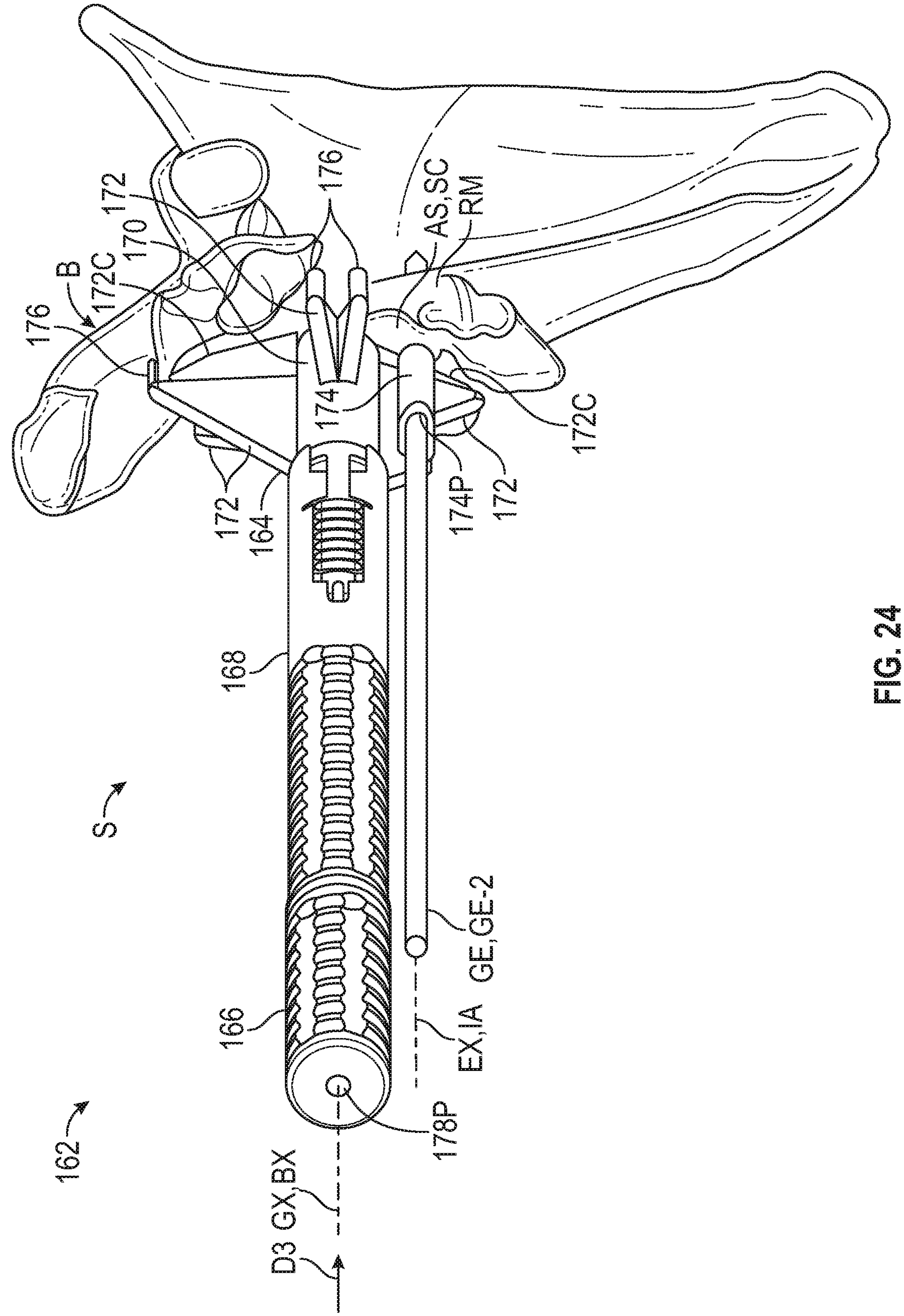
FIGS. 24-25 disclose a surgical guide positioned relative to a bone and positioning of one or more guide element according to an implementation.

Referring to FIG. 24, with continuing reference to FIG. 23, the transfer guide 162 may be positioned at a surgical site S at step 190B. In implementations, step 190B may include positioning the guide 162 on an articular surface AS of a bone B. The bone B and articular surface AS may be associated with a joint, including any of the joints disclosed herein, such as a scapula associated with a shoulder joint. The articular surface AS may be associated with a glenoid of the patient. The articular surface AS may be associated with a surface contour SC of the bone B.

The guide 162 may include a patient-specific locating component 164, a sleeve 168 releasably securable to the locating component 164 and/or a bushing 166 insertable in the sleeve 168 and/or the locating component 164. The locating component 164 may include a guide (e.g., main) body 170 and a plurality of locating members (e.g., arms) 172 that may extend from a periphery of the main body 170. The locating arms 172 may have respective patient-specific contact surfaces 172C that may be dimensioned to follow the surface contour SC of the articular surface AS. Step 190B may include moving the guide 162 in a third direction D3 and positioning the contact surfaces 172C in abutment with the articular surface AS to establish a patient-specific position of the locating component 164, which may be specified in a surgical plan 33 for a patient (e.g., FIG. 2).

The locating component 164 may include at least one or more overhangs 176. Each overhang 176 may extend from an end portion of a respective one of the locating arms 172. Step 190B may include positioning the overhang(s) 176 in engagement with a rim RM of the bone B to set a position of the locating component 164 on the articular surface AS.

In the implementation of FIG. 20, step 190B may include inserting the bushing 166 at least partially through the sleeve passageway 180P in the sleeve 168 and the locating passageway 170P in the locating component 164 such that the bushing 166 may be situated above (e.g., proximal to) the locating component 164 relative to the articular surface AS. Situating the bushing 166 above the articular surface AS may improve seating the locating component 164 on the bone B. A distal end of the bushing 166 may be spaced apart from the articular surface AS when the guide 162 may be positioned on the bone B. The guide 162 may be assembled prior and/or subsequent to seating the locating component 164 on the bone B.

At step 190C, one or more guide elements GE may be positioned in the bone B. The guide elements GE may including any of the guide elements disclosed herein. Step 190C may include positioning a (e.g., second) guide element GE-2 through the locating component 164 and into the articular surface AS of the bone B. Step 190C may include positioning the second guide element GE-2 through a selected one of the guide passages 174P of the locating component 164 and then driving the second guide element GE-2 into the articular surface AS of the bone B, which may be associated with a predetermined position and/or trajectory specified in the surgical plan 33. Step 190C may include inserting the second guide element GE-2 through a guide passage 174P in an extension 174 from the respective locating arm 172.

The locating component 164 may include a plurality of extensions 174 that may extend circumferentially from one or more of the locating arms 172 relative to the guide axis GX of the locating component 164. Each of the extensions 174 may include a respective guide passage 174P associated with a position of a respective one of the implant passages 159 (e.g., FIG. 35). The guide passages 174P may be circumferentially offset at different distances from the respective locating arms 172 relative to the guide axis GX based on the circumferential positions of the implant passages 159 relative to the implant axis X of the implant 150. An extension (e.g., passage) axis EX of each guide passage 174P may be established based on the associated insertion axis IA of the guide element GE as specified in the surgical plan 33 (see also FIG. 10).

Step 190C may include inserting the second guide element GE-2 through a guide passage 174P in an extension 174 from the respective locating arm 172. The guide passage 174P may be situated relative to the bone B such that the insertion axis IA of the second guide element GE-2 may be substantially aligned with the insertion axis IA specified in the surgical plan 33.

The bushing passage 178P and the guide passage(s) 174P may extend along respective bushing and extension passage axes BX, EX (see also FIGS. 10 and 20). The passage axes BX, EX and/or overhangs 176 may be substantially parallel to each other in an assembled configuration (e.g., FIGS. 24-25 and 27), which may facilitate removal of the guide 162 from the bone B without removing the respective guide element(s) GE. In implementations, the locating component 164 may include a plurality of overhangs 176, which may be circumferentially distributed about the main body 170. The overhangs 176 may be dimensioned such that the locating component 164 may be removable from the articular surface AS without removing the first and/or second guide elements GE-1, GE-2 from the bone B.

Figure 25:
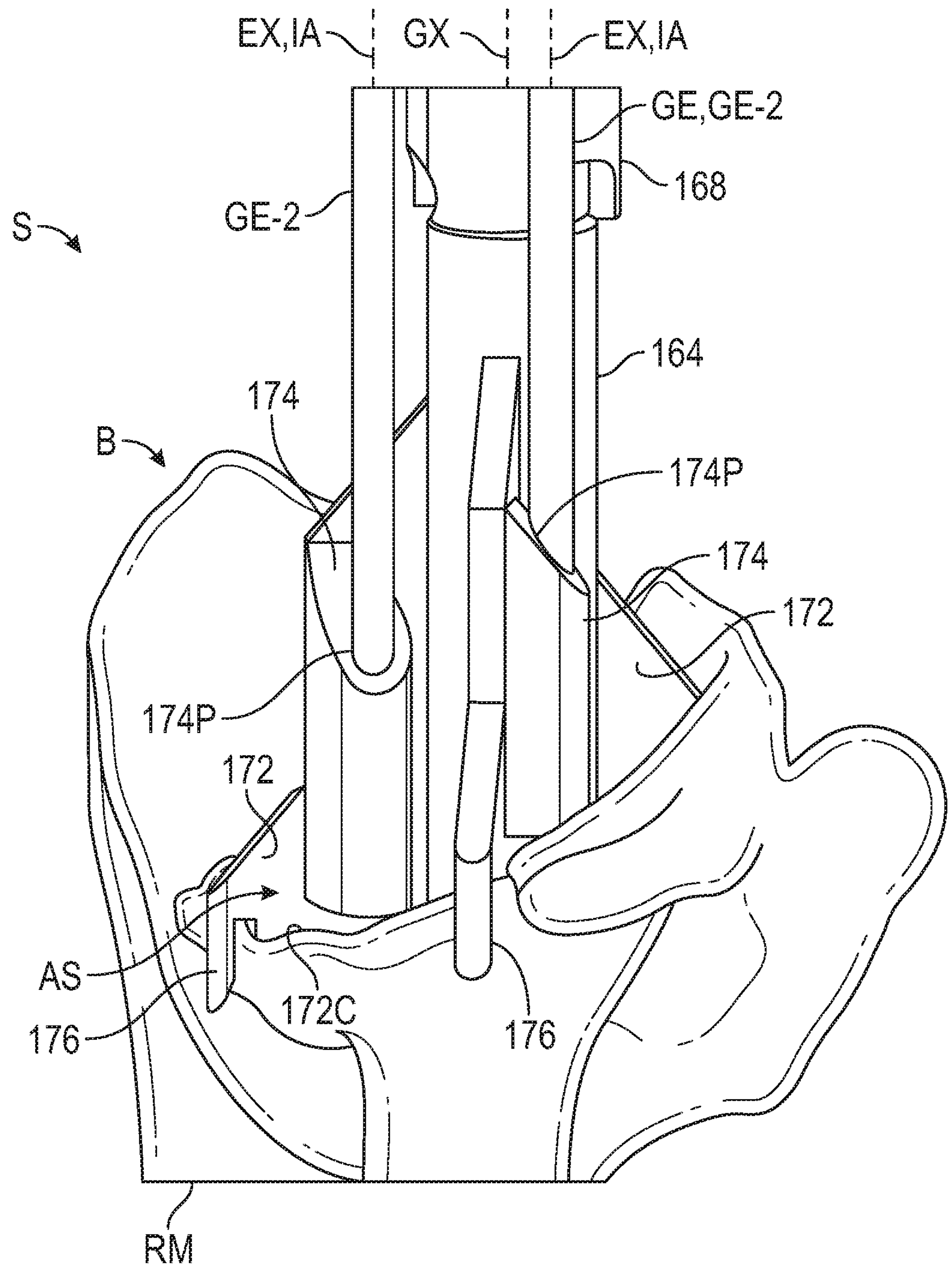

In the implementation of FIG. 25, the surgeon may insert the guide element GE-2 in a selectable one of the guide passages 174P, which may be associated with different extensions 174 and/or different positions relative to the guide axis GX. The guide passages 174P may be arranged to drive the guide element GE-2 into the bone B at different positions and/or trajectories relative to the articular surface AS.

Figure 26:
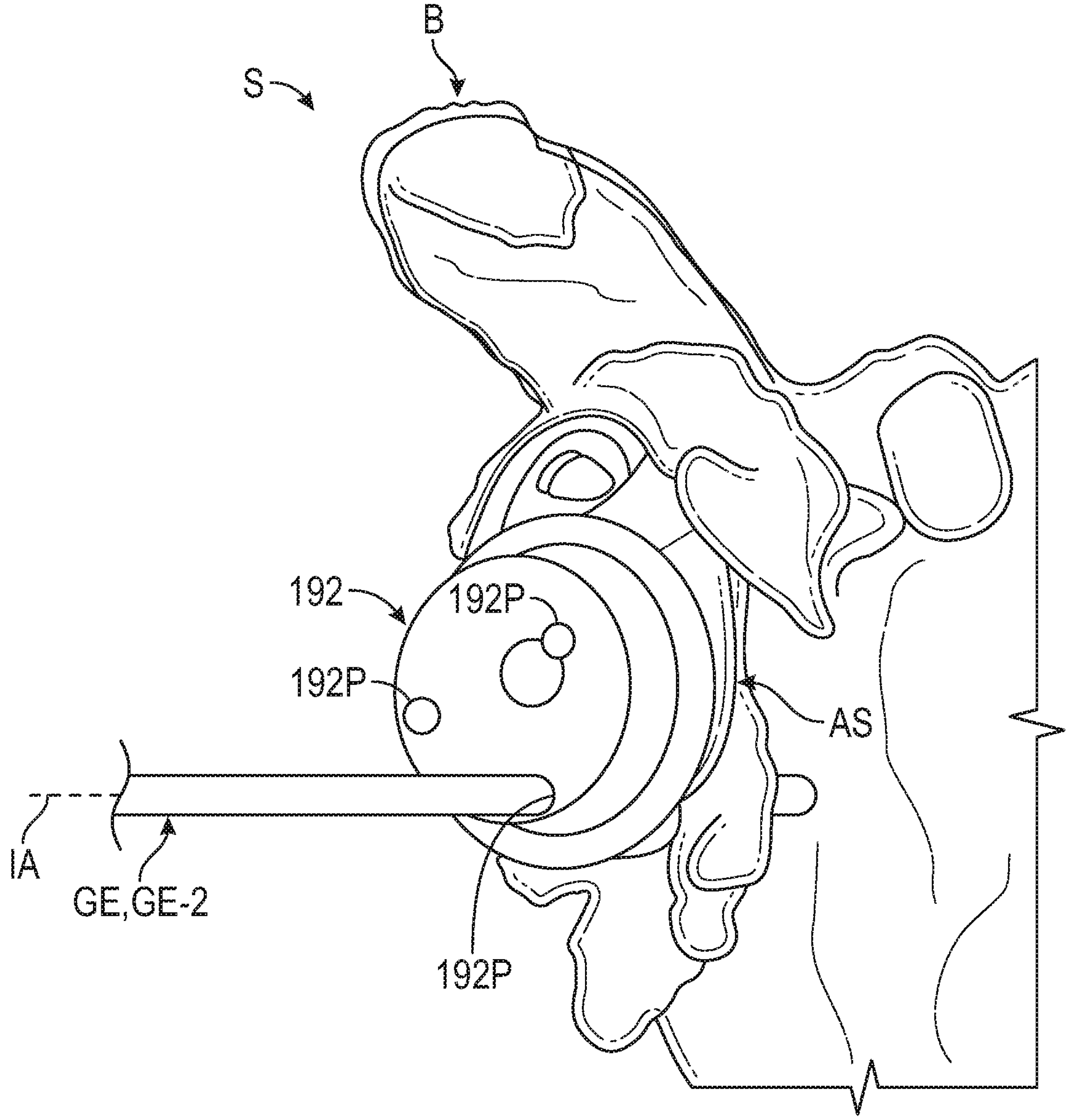
FIG. 26 discloses a trial implant positioned relative to the bone of FIG. 24 using a guide element.

Referring to FIG. 26, with continuing reference to FIGS. 23-24, a fit of the implant 150 may be checked (e.g., verified) at step 190D. Step 190D may include checking a fit of a rear (e.g., patient-specific) surface 151B of the implant 150 on the articular surface AS of the bone B. Step 190C may include removing the guide 162 at least partially from the articular surface AS and then translating a trial implant 192 along at least one of the (e.g., first and second) guide elements GE such that a rear (e.g., patient-specific) surface of the trial implant 192 may abut the articular surface AS. The patient-specific surface of the trial implant 192 may have a substantially similar geometry to the patient-specific surface of the implant 150.

The trial implant 192 may include one or more trial passages 192P. Each trial passage 192P may be dimensioned to receive a respective guide element GE. The trial passages 192P may be associated with the position and/or orientation of respective implant passages 159 of the implant 150 (e.g., FIG. 35).

If the surgeon is dissatisfied with the fit of the trial implant 192, the surgeon may remove the guide element GE-2 and may position the guide element GE-2 (or a different guide element) in another one of the guide passages 174P of the locating component 164 and into the bone B at step 190C. The surgeon may recheck the fit of the trial implant 192, which may improve seating the implant 150 relative to the bone B according to the surgical plan 33.

Figure 27:
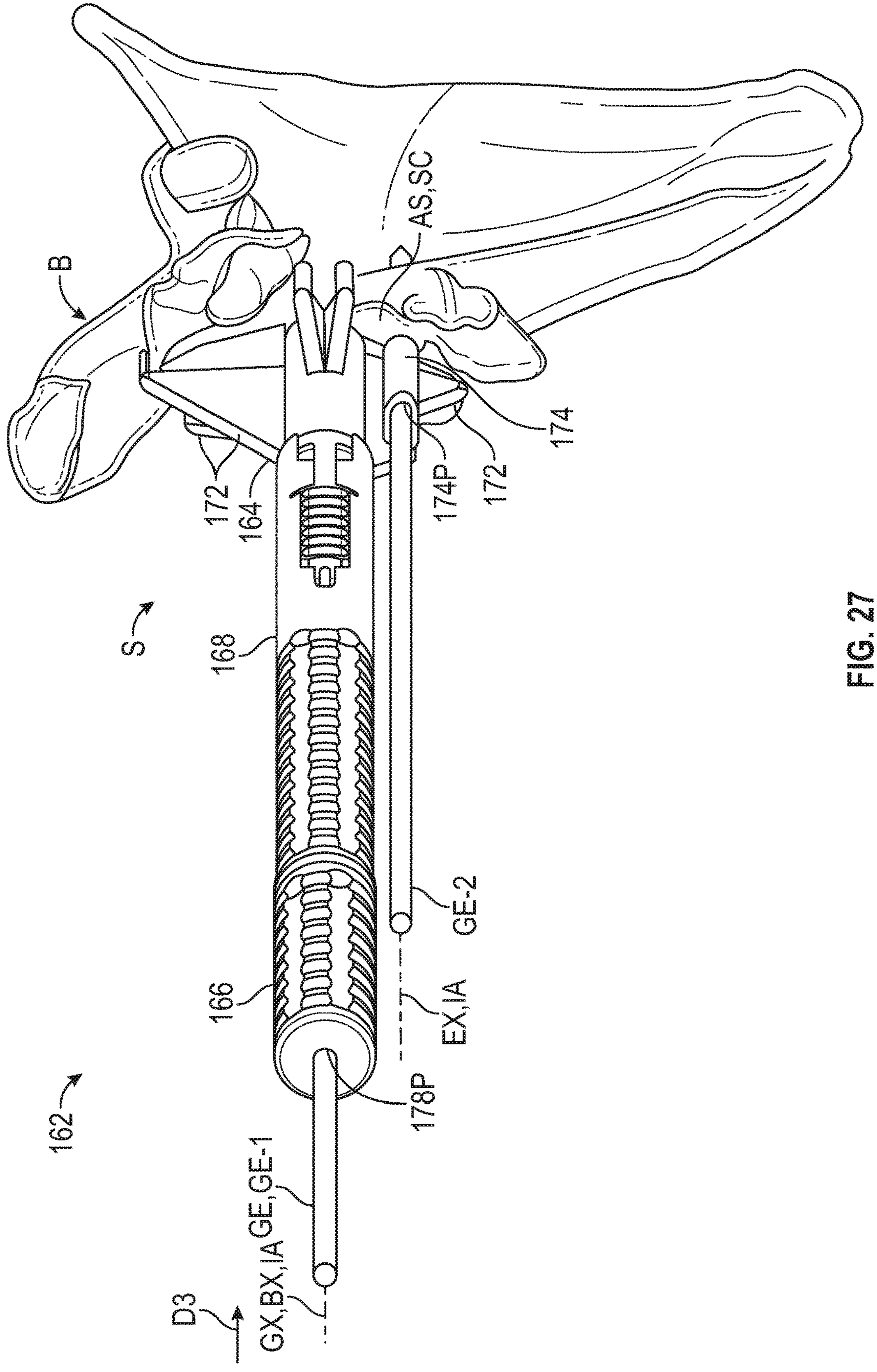
FIG. 27 discloses positioning of one or more guide element using the surgical guide of FIG. 24.

Referring to FIG. 27, with continuing reference to FIGS. 23-24, one or more (e.g., additional) guide elements GE may be positioned in the bone B at step 190E. Step 190E may include positioning the guide 162 onto the bone B by translating the same extension 174 along the second guide element GE-2 to seat the guide 162 in substantially the same position prior to removing the guide 162 from the articular surface AS.

Step 190E may include positioning a (e.g., first) guide element GE-1 through the locating component 164 and into the articular surface AS of the bone B. The guide elements GE-1, GE-2 may be inserted at different positions along the bone B. Step 190E may include positioning the first guide element GE-1 through the bushing passage 178P of the bushing 166 and then driving the guide element GE-1 into the articular surface AS of the bone B, which may be associated with a predetermined position and/or trajectory specified in the surgical plan 33.

Figure 28:
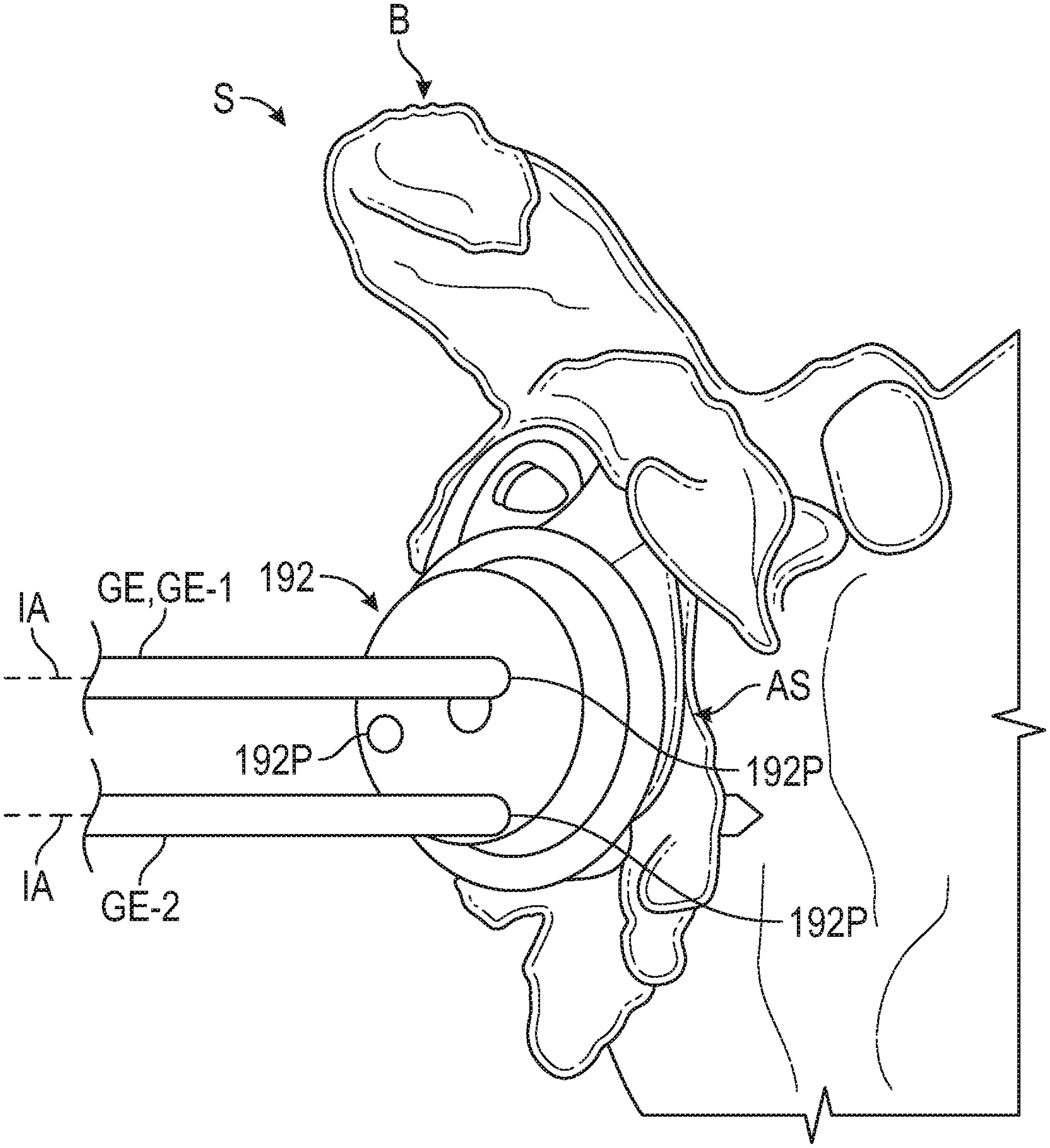
FIG. 28 discloses the trial implant of FIG. 26 positioned relative to the bone of FIG. 24 using guide elements.

Referring to FIG. 28, with continuing reference to FIGS. 23 and 27, a fit of the implant 150 may be checked (e.g., verified) at step 190F. Step 190F may include checking the fit of the patient-specific surface of the implant 150 on the articular surface AS of the bone B. Step 190F may include removing the guide 162 at least partially from the articular surface AS, inserting at least two guide elements GE into respective trial passages 192P of the trial implant 192, and then translating the trial implant 192 along the guide elements GE such that the patient-specific surface of the trial implant 192 may abut the articular surface AS. Verifying the fit of the trial implant 192 using more than one guide element GE may improve accuracy in positioning the implant 150 on the bone B according to the surgical plan 33.

Figure 29:
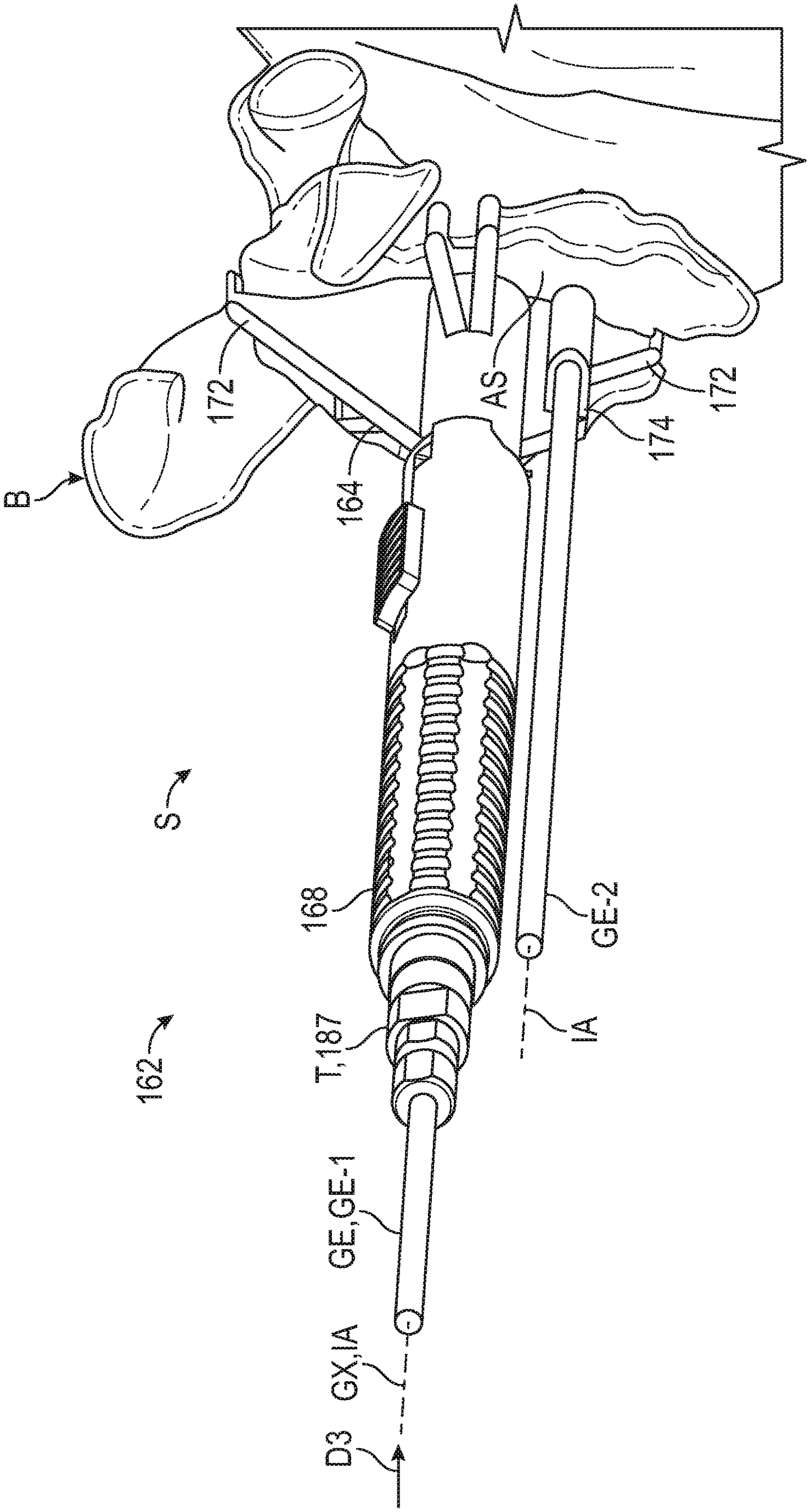
FIGS. 29-30 disclose removal of bone with a surgical tool using the surgical guide of FIG. 24.
Figure 30:
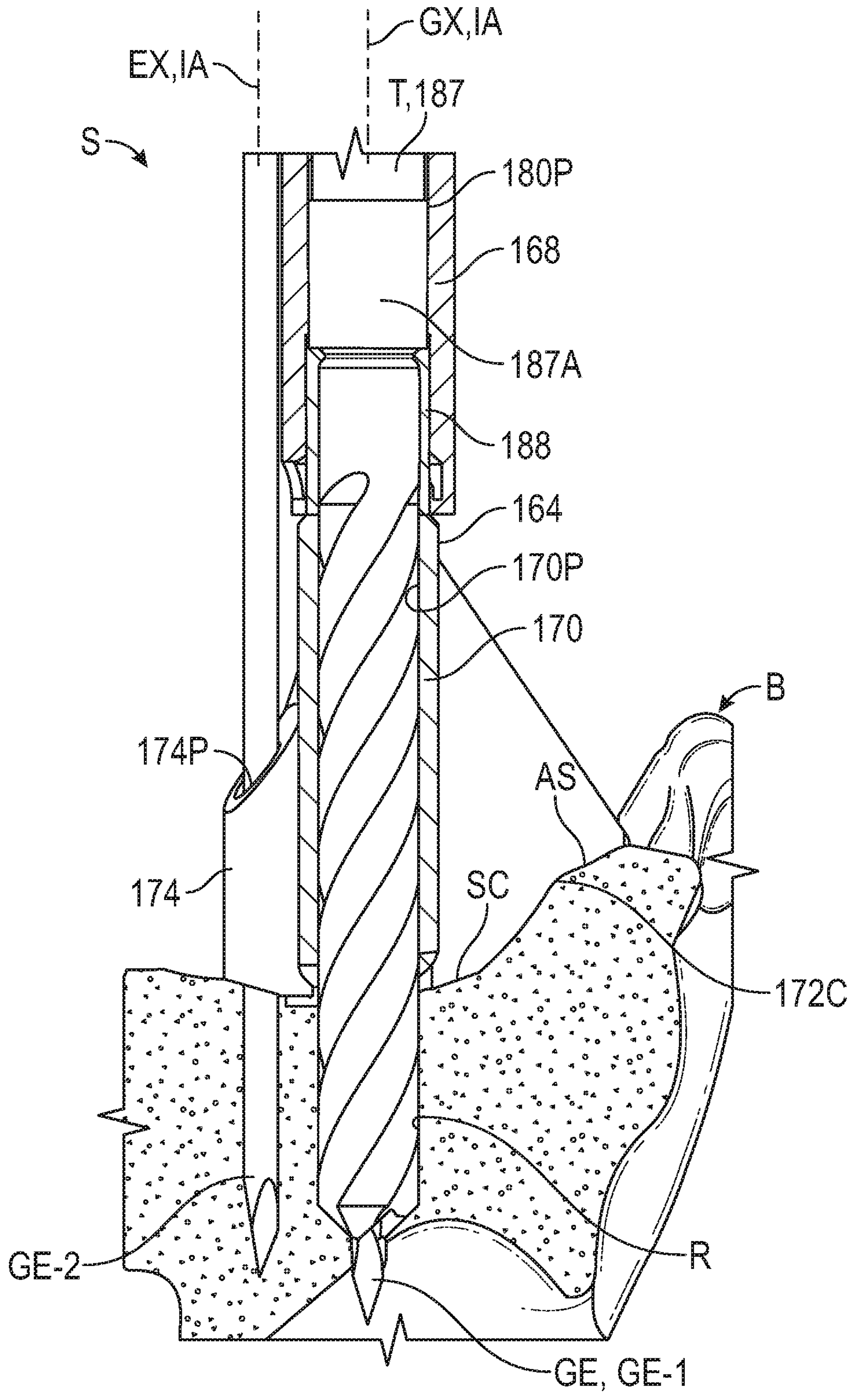
Figure 31:
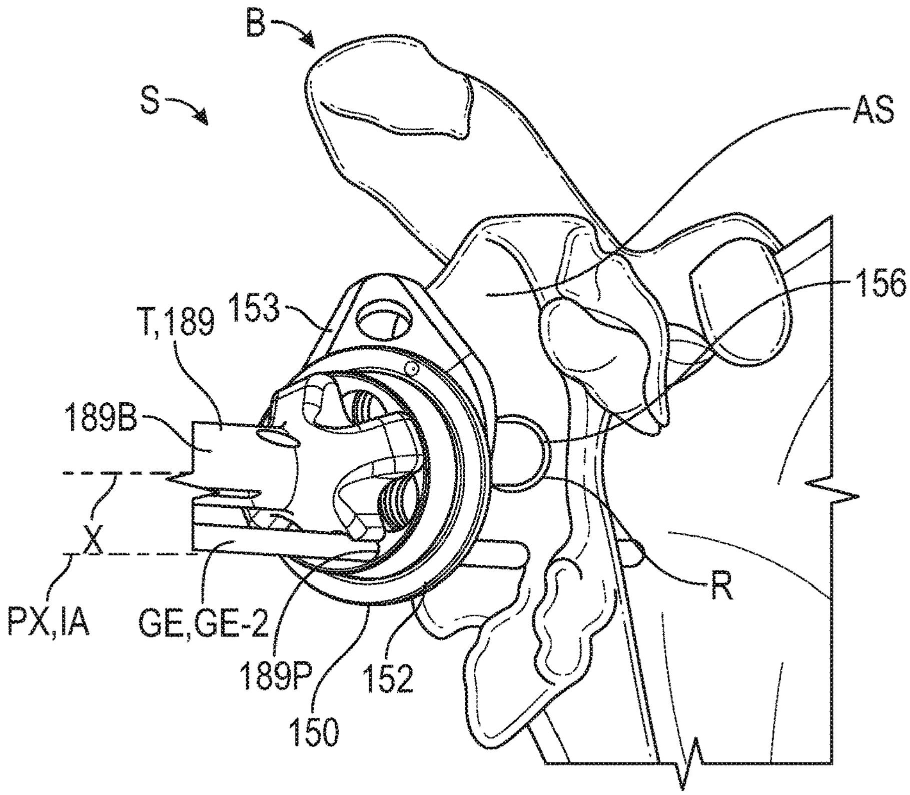
FIGS. 31-34 disclose positioning an implant on the bone using another surgical tool.
Figure 32:
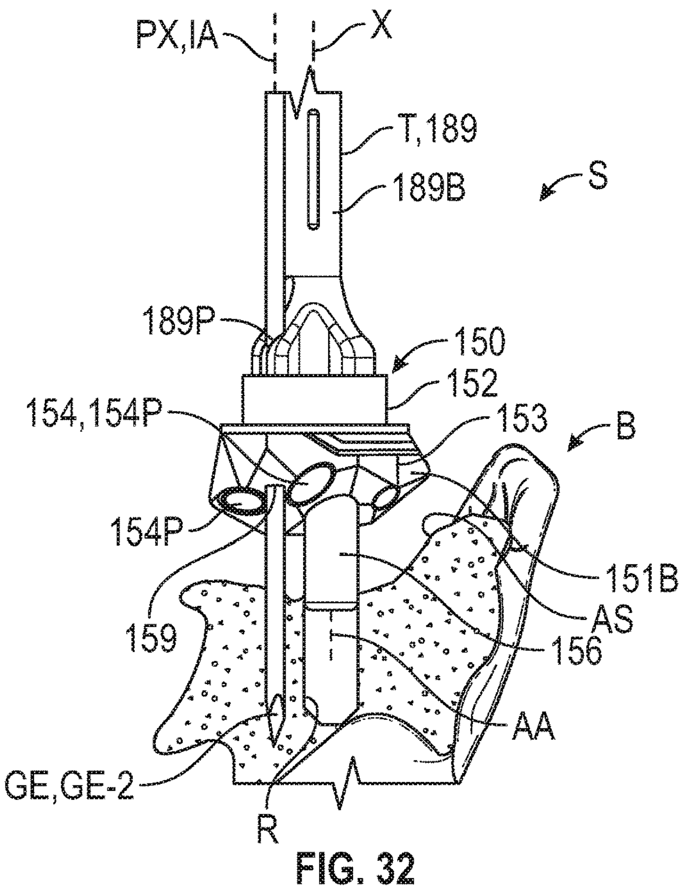

Referring to FIGS. 29-30, with continuing reference to FIGS. 23 and 27, at least one surgical tool (e.g., instrument) T may be guided using the guide 162 at step 190G. Step 190G may include removing at least the bushing 166 from the locating component 164 without removing the first guide element GE-1 from the bone B. Step 190G may include removing the trial implant 192. Step 190G may include positioning the locating component 164 onto the bone B by translating the same extension 174 along the second guide element GE-2 to seat the locating component 164 in substantially the same position prior to removing the guide 162 from the articular surface AS.

The surgical tool T may be a drill 187. The drill 187 may be cannulated. Step 190G may include guiding the drill 187 along the first guide element GE-1 to form a recess (e.g., hole) R in the articular surface AS (FIG. 30). An abutment 187A of the drill 187 may be moved into engagement with the depth stop 188 to limit translation of the drill 187 along the first guide element GE-1 (FIG. 30). The depth stop 188 may limit an insertion depth of the drill 187 for establishing a depth of the recess R according to the surgical plan 33.

Referring to FIGS. 31-34, with continuing reference to FIGS. 23 and 29-30, the implant 150 may be positioned at step 190H. Step 190H may include at least partially inserting a fixation member 156 of the implant 150 into the recess R. Step 190G may include positioning a rear (e.g., patient-specific) surface 151B of the implant 150 on the articular surface of the bone B by translating the implant 150 along the second guide element GE-2. The first guide element GE-1 may be removed from the bone B prior to step 190H. Positioning the implant 150 may include inserting the second guide element GE-2 through a selected one of the implant passages 159 and then into the articular surface AS to limit relative movement between the implant 150 and the bone B. The implant 150 may be translated along the second guide element GE-2 such that the patient-specific surface 151B of the implant 150 may abut the articular surface AS of the bone B in a patient-specific position and/or orientation (FIGS. 33-34), which may be specified in a surgical plan 33 associated with the patient.

Step 190H may include using a surgical tool T to position the implant 150 relative to the bone B. In implementations, the surgical tool T may be an impactor 189. Step 190H may include translating the implant 150 and the impactor 189 together along the second guide element GE-2 and then impacting, using the impactor 189, the fixation member 156 of the implant 150 into the recess R. The impactor 189 may be adapted to position the implant 150 relative to the bone B. The impactor 189 may include an impactor body 189B having one or more impactor passage(s) 189P. The impactor 189 may be dimensioned such that the impactor passage 189P may be substantially aligned with the implant passage 159 in an assembled configuration.

Figure 33:
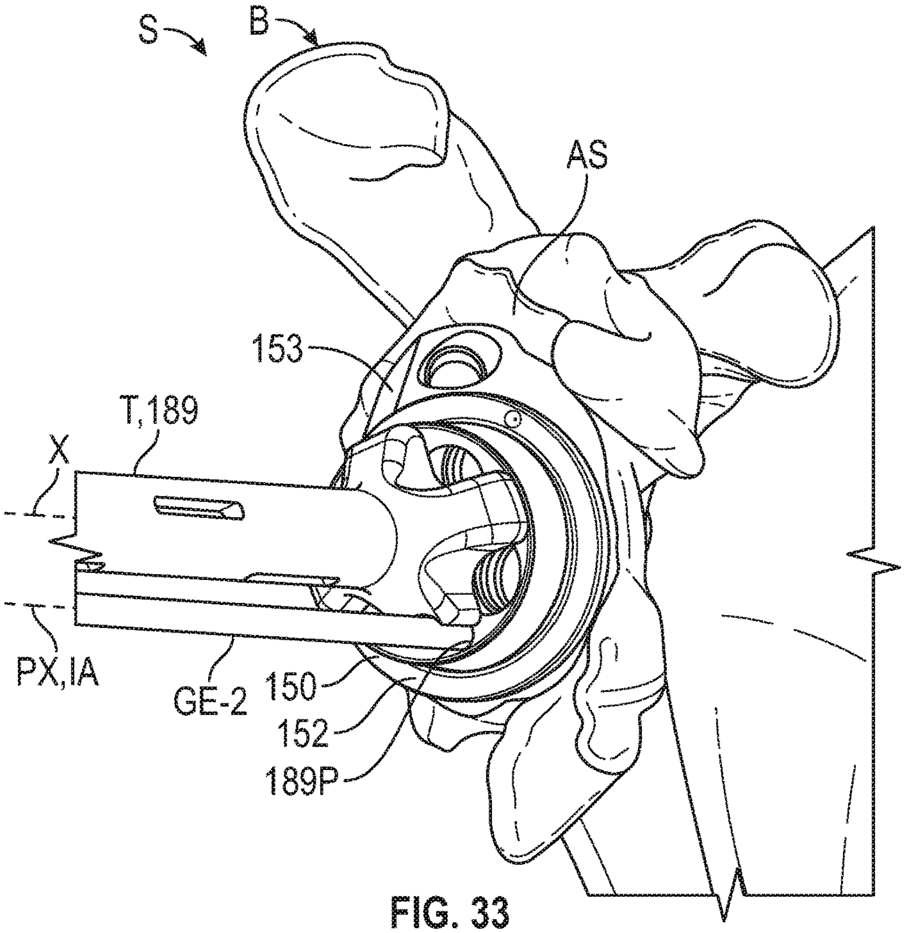
Figure 34:
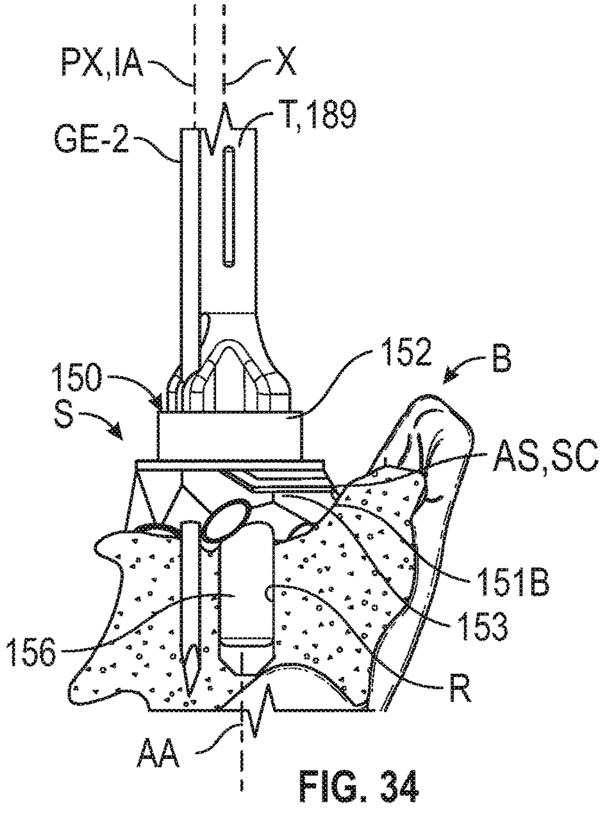
Figure 35:
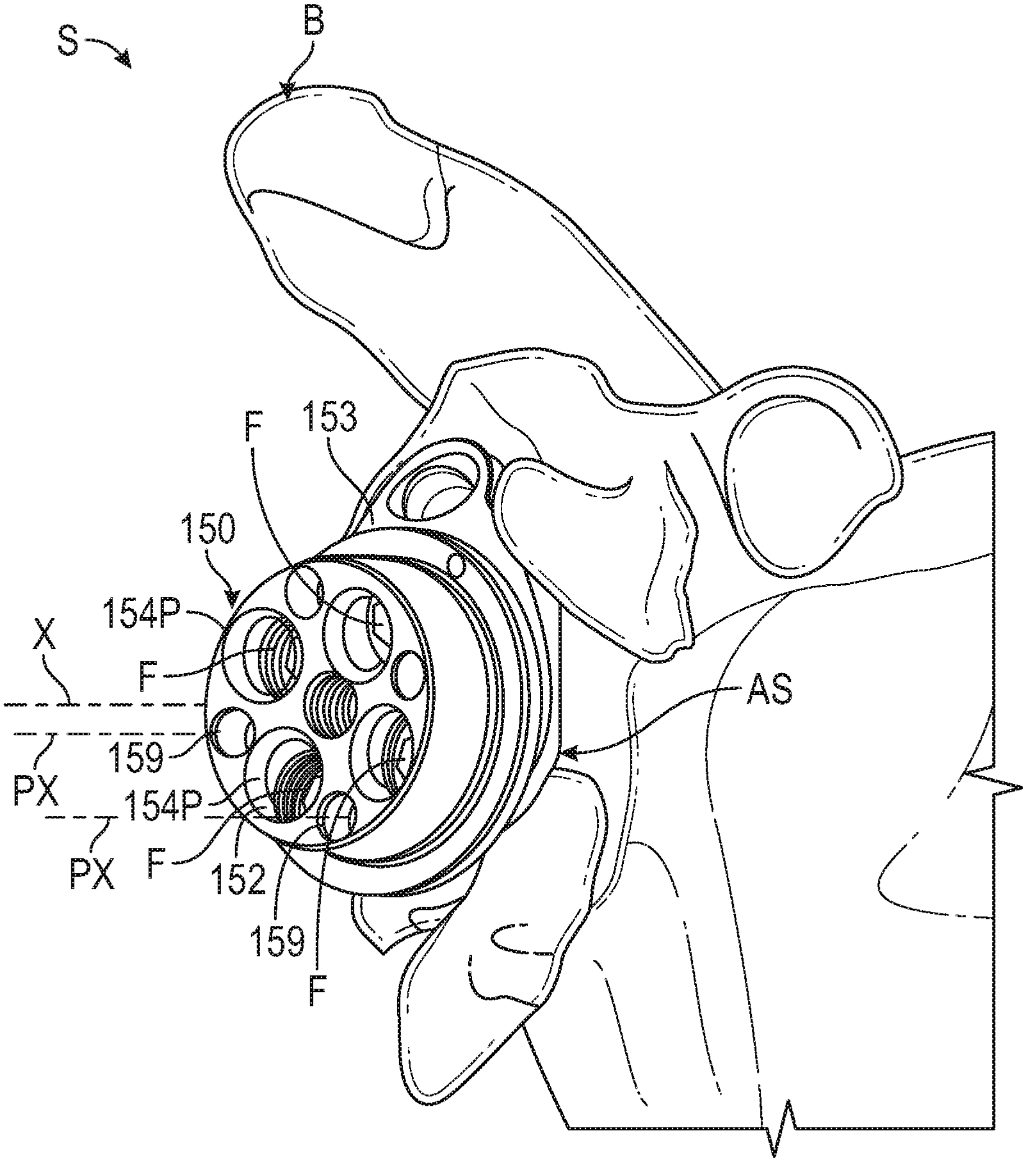
FIG. 35 discloses the implant of FIGS. 31-34 secured to the bone.

Referring to FIG. 35, with continuing reference to FIGS. 23 and 33-34, the guide element(s) GE and surgical tool(s) T may be removed from the surgical site S at step 190J. The implant 150 may be positioned on the bone B in a patient-specific position and/or orientation, which may be specified in the surgical plan 33. The patient-specific position of the implant 150 may be established based on use of the transfer guide 162 to substantially achieve alignment of the insertion axes IA of the physical guide elements GE relative to the bone B according to the positions and trajectories of the insertion axes IA set or otherwise defined in the surgical plan 33.

At step 190T, the implant 150 may be secured to the bone B with one or more fasteners F. The fastener(s) F may be positioned through the implant 150 and into the bone B. Step 190T may occur such that the implant 150 may be secured in a position relative to the bone B that may substantially correspond to a patient-specific position specified in the surgical plan 33.

The novel devices and methods of this disclosure provide improved accuracy in positioning orthopaedic implants for treating a patient. Transfer guides may be generated based on parameters specified in surgical plans associated with respective patients to position the respective implant in a patient-specific position, which may improve healing and achievement of range of motion and achieving acts of daily living goals. The discloses guides may incorporate patient-specific locating components to position the respective implant in a patient-specific position. The locating component may be utilized with one or more reusable components, which may reduce cost and complexity in providing the guide.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for an orthopaedic procedure comprising:

a bushing including a bushing passage dimensioned to receive a first guide element for guiding a surgical instrument; and a locating component comprising:

a main body including a locating passageway extending along a guide axis, the locating passageway dimensioned to receive the bushing to set a trajectory of the bushing passage;

locating arms extending from the main body, the locating arms including respective patient-specific contact surfaces dimensioned to follow a bone contour; and at least one extension that extends circumferentially from a respective one of the locating arms relative to the guide axis, the at least one extension including a guide passage dimensioned to receive a second guide element, and a position of the guide passage in the at least one extension is based on a position of an implant passage of an implant associated with a surgical plan.

2. The system as recited in claim 1, wherein the implant is patient-specific.

3. The system as recited in claim 1, further comprising:

an impactor adapted to position an implant relative to bone, the impactor including an impactor body having an impactor passage; and wherein the impactor is dimensioned such that the impactor passage is substantially aligned with the implant passage in an assembled configuration.

4. The system as recited in claim 1, wherein the at least one extension is dimensioned to follow an arc path about the guide axis, and the position of the guide passage is established along the arc path.

5. The system as recited in claim 4, wherein the at least one extension includes a plurality of extensions, and the arc paths of the respective extensions have a common radius.

6. The system as recited in claim 4, wherein positions of the respective locating arms relative to the main body are set prior to the positions of the guide passages in the extensions.

7. The system as recited in claim 1, wherein the bushing passage and the at least one guide passage extend along respective passage axes, and the passage axes are substantially parallel to each other in an assembled configuration.

8. The system as recited in claim 1, further comprising:

a sleeve including a sleeve passageway;

wherein the sleeve is releasably securable to a proximal portion of the main body;

wherein the sleeve passageway and the locating passageway are at least partially aligned with each other in an assembled configuration; and wherein the bushing is at least partially insertable through the sleeve passageway and the locating passageway in the assembled configuration to set the trajectory of the bushing passage.

9. The system as recited in claim 1, further comprising:

at least one overhang extending from an end portion of a respective one of the locating arms; and wherein the at least one overhang is dimensioned to contact a non-articular surface of a bone to limit movement of the locating component when the contact surfaces are seated on an articular surface of a bone associated with the bone contour.

10. The system as recited in claim 1, wherein the at least one extension is cantilevered from the respective locating arm.

11. The system as recited in claim 1, wherein the at least one extension has an arcuate geometry dimensioned to follow a circumferential path about the guide axis.

12. The system as recited in claim 1, wherein the locating component is monolithic.

13. A system for an orthopaedic procedure comprising:

a locating component including a main body, a plurality of locating arms extending from a periphery of the main body, and a locating passageway in the main body, wherein the locating arms include respective patient-specific contact surfaces dimensioned to follow a bone contour of a patient;

a sleeve releasably securable to the locating component, the sleeve including a sleeve passageway; and a bushing including a bushing passage dimensioned to receive a first guide element for guiding a surgical instrument, the bushing insertable in the sleeve passageway and the locating passageway to set a trajectory of the bushing passage; and wherein a depth stop is established by the locating component within the sleeve passageway, and the depth stop is dimensioned to limit insertion of a surgical tool through the locating passageway.

14. The system as recited in claim 13, wherein:

the surgical tool is slidably receivable through the sleeve passageway such that an abutment of the surgical tool engages the depth stop to limit insertion of the surgical tool through the locating passageway.

15. The system as recited in claim 13, wherein the surgical instrument is a drill.

16. The system as recited in claim 13, further comprising: a twist-lock mechanism adapted to releasably secure the sleeve and the locating component to each other.

17. The system as recited in claim 16, wherein: the twist-lock mechanism includes a push-lock adapted to selectively lock the locating component and sleeve together.

18. The system as recited in claim 13, wherein the bushing comprises a first type of material, and the locating component comprises a second type of material that differs from the first type of material.

19. The system as recited in claim 13, wherein the main body of the locating component has a tubular geometry.

20. The system as recited in claim 13, wherein the locating component is monolithic.

* * * * *